(12) United States Patent
Tsals

(10) Patent No.: US 8,556,861 B2
(45) Date of Patent: Oct. 15, 2013

(54) METHODS AND DEVICES FOR INTRADERMAL INJECTION

(75) Inventor: Izrail Tsals, Newtown, PA (US)

(73) Assignees: SID Technologies, LLC, Newton, PA (US); Program for Appropriate Technology in Health, Seattle, WA (US)

( * ) Notice: Subject to any disclaimer, the term of this patent is extended or adjusted under 35 U.S.C. 154(b) by 362 days.

(21) Appl. No.: 12/597,103

(22) PCT Filed: Apr. 23, 2008

(86) PCT No.: PCT/US2008/061331
§ 371 (c)(1),
(2), (4) Date: Oct. 22, 2009

(87) PCT Pub. No.: WO2008/131440
PCT Pub. Date: Oct. 30, 2008

(65) Prior Publication Data
US 2010/0137831 A1    Jun. 3, 2010

Related U.S. Application Data

(60) Provisional application No. 60/925,609, filed on Apr. 23, 2007, provisional application No. 60/928,423, filed on May 10, 2007.

(51) Int. Cl.
*A61M 5/00* (2006.01)

(52) U.S. Cl.
USPC ............ 604/187; 604/192; 604/198; 604/506

(58) Field of Classification Search
USPC ......... 604/110, 115, 136–137, 157, 187, 192, 604/198, 263, 500, 506
See application file for complete search history.

(56) References Cited

U.S. PATENT DOCUMENTS

| | | |
|---|---|---|
| 2,701,566 A | 2/1955 | Krug |
| 3,324,854 A | 6/1967 | Weese |
| 4,332,248 A | 6/1982 | DeVitis |
| 4,393,870 A | 7/1983 | Wagner |
| 4,631,057 A | 12/1986 | Mitchell |

(Continued)

FOREIGN PATENT DOCUMENTS

| | | |
|---|---|---|
| EP | 0457477 A1 | 11/1991 |
| EP | 0702973 A2 | 3/1996 |

(Continued)

OTHER PUBLICATIONS

Int'l Application No. PCT/US11/28072 filed Mar. 11, 2011.

(Continued)

*Primary Examiner* — Theodore Stigell
(74) *Attorney, Agent, or Firm* — Panitch Schwarze Belisario & Nadel LLP

(57) ABSTRACT

Devices and methods for intradermal (ID) administration of diagnostic and therapeutic agents, vaccines and other compounds into the dermal layer of the skin are disclosed. The devices and the methods simplify the ID injection process and increase the consistency of the placement of the needle tip in the dermal space close to the skin surface allowing for a shallow cannula placement in the dermis. Furthermore, the devices and methods broaden the number of sites suitable for ID injection and make the ID injection possible with limited training.

33 Claims, 34 Drawing Sheets

(56) References Cited

U.S. PATENT DOCUMENTS

| | | | |
|---|---|---|---|
| 4,737,144 A | 4/1988 | Choksi | |
| 4,747,837 A | 5/1988 | Hauck | |
| 4,801,295 A | 1/1989 | Spencer | |
| 4,850,996 A | 7/1989 | Cree | |
| 4,958,625 A | 9/1990 | Bates et al. | |
| 4,998,920 A | 3/1991 | Johnson | |
| 5,053,018 A | 10/1991 | Talonn et al. | |
| 5,108,378 A * | 4/1992 | Firth et al. | 604/192 |
| 5,364,362 A * | 11/1994 | Schulz | 604/115 |
| 5,437,640 A | 8/1995 | Schwab | |
| 5,496,288 A | 3/1996 | Sweeney | |
| 5,527,287 A | 6/1996 | Miskinyar | |
| 5,669,888 A | 9/1997 | Trapp | |
| 5,893,845 A | 4/1999 | Newby et al. | |
| 6,200,291 B1 | 3/2001 | Di Pietro | |
| 6,494,865 B1 | 12/2002 | Alchas | |
| 6,569,123 B2 | 5/2003 | Alchas et al. | |
| 6,666,844 B1 * | 12/2003 | Igo et al. | 604/115 |
| 6,689,118 B2 | 2/2004 | Alchas et al. | |
| 6,776,776 B2 | 8/2004 | Alchas et al. | |
| 7,052,483 B2 | 5/2006 | Wojcik | |
| 8,083,715 B2 * | 12/2011 | Sonoda et al. | 604/115 |
| 2002/0077599 A1 | 6/2002 | Wojcik | |
| 2002/0193744 A1 | 12/2002 | Alesi et al. | |
| 2003/0050602 A1 | 3/2003 | Pettis et al. | |
| 2003/0093032 A1 | 5/2003 | Py et al. | |
| 2003/0199822 A1 | 10/2003 | Alchas et al. | |
| 2004/0147901 A1 | 7/2004 | Py et al. | |
| 2006/0079920 A1 | 4/2006 | Schraga | |
| 2007/0118077 A1 | 5/2007 | Clarke et al. | |

FOREIGN PATENT DOCUMENTS

| | | | |
|---|---|---|---|
| EP | 2139543 A1 | 1/2010 | |
| FR | 2612401 A1 | 9/1988 | |
| JP | 02-046861 A | 2/1990 | |
| JP | 08-107933 A | 4/1996 | |
| JP | 2010524646 T | 7/2010 | |
| WO | 9741907 A2 | 11/1997 | |
| WO | 2006052737 A1 | 5/2006 | |
| WO | 2008131440 A1 | 10/2008 | |
| WO | 2010077596 A1 | 7/2010 | |
| WO | 2011011697 A1 | 1/2011 | |

OTHER PUBLICATIONS

Int'l Preliminary Report on Patentability Issued May 8, 2007 in Int'l Application No. PCT/US05/039979; Written Opinion.
Int'l Preliminary Report on Patentability Issued Aug. 14, 2009 in Int'l Application No. PCT/US08/61331.
Int'l Search Report issued Oct. 27, 2010 in Int'l Application No. PCT/US2010/043071; Written Opinion.
Int'l Search Report issued on Mar. 23, 2006 in Int'l Application No. PCT/US05/39979.
Int'l Search Report issued on Sep. 16, 2008 in Int'l Application No. PCT/US08/61331.
International Search Report Issued Mar. 29, 2010 in Int'l Application No. PCT/US2009/066960; Written Opinion.
U.S. Appl. No. 13/057,006, filed Feb. 1, 2011.
U.S. Appl. No. 60/928,423, filed May 10, 2007.
Written Opinion issued on Sep. 16, 2008 in Int'l Application No. PCT/US08/61331.
Office Action issued May 15, 2012 in JP Application No. 2010-506461 (with English translation of relevant portions).
Int'l Preliminary Report on Patentability issued Apr. 9, 2012 in Int'l Application No. PCT/US10/43071.
International Search Report Issued Aug. 4, 2011 in Int'l Application No. PCT/US2011/028072.
U.S. Appl. No. 13/583,096 by TSALS, filed Sep. 6, 2012.
Int'l Preliminary Report on Patentability issued Sep. 27, 2012 in Int'l Application No. PCT/US2011/028072.
Office Action issued Apr. 30, 2013 in JP Application No. 2012-521832.
Office Action issued Apr. 15, 2013 in U.S. Appl. No. 13/057,006.
Office Action issued Apr. 24, 2013 in U.S. Appl. No. 13/583,096.

* cited by examiner

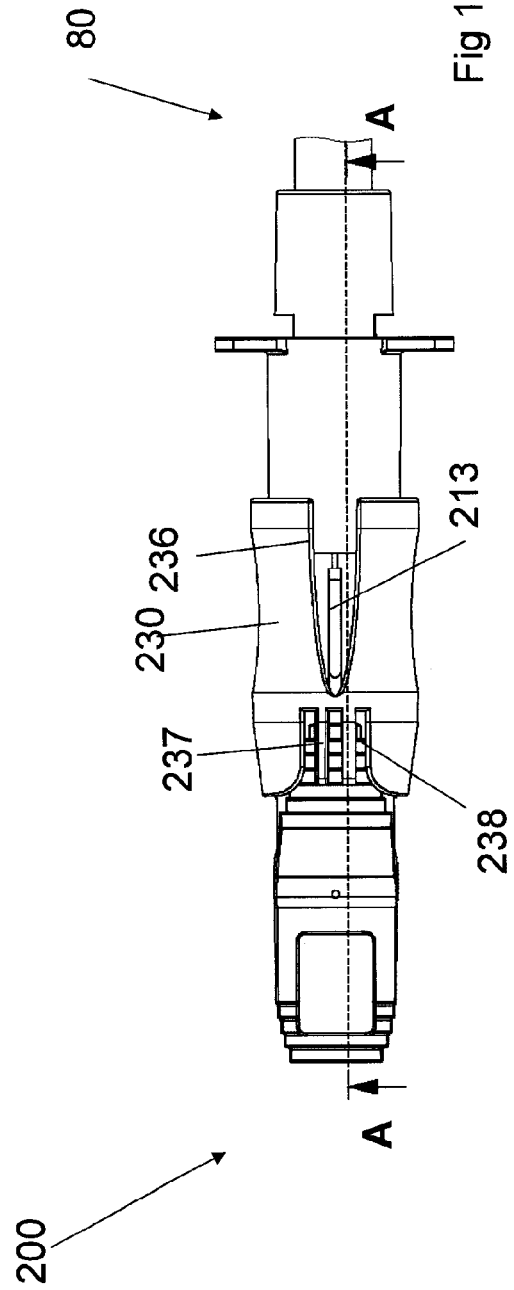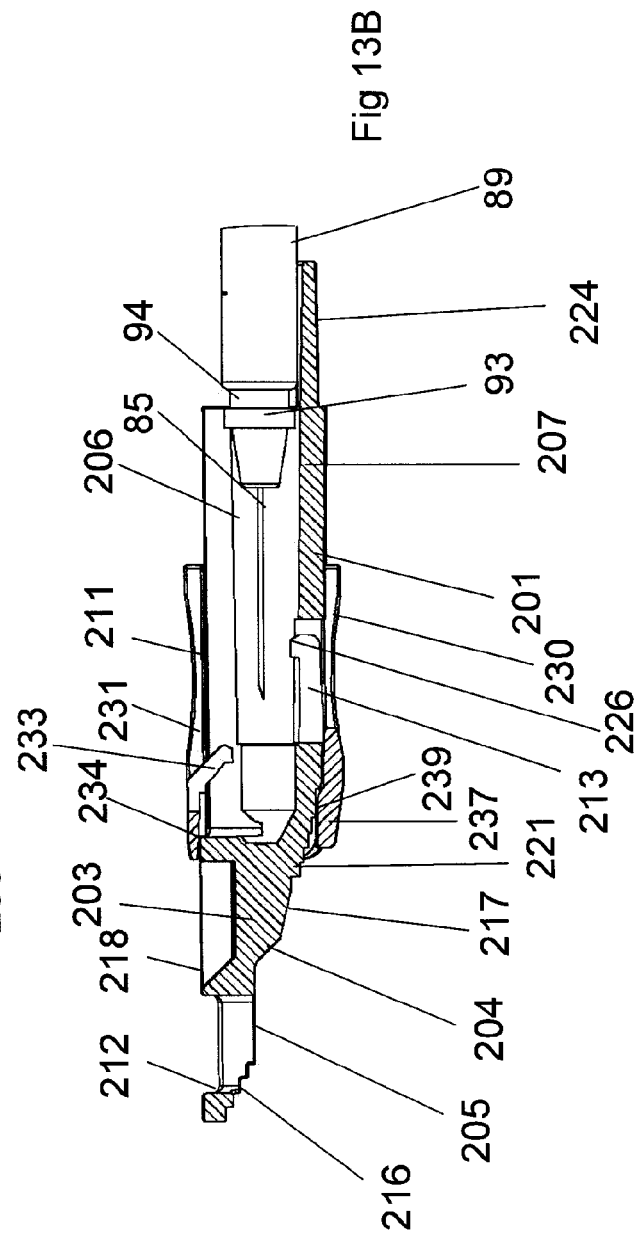

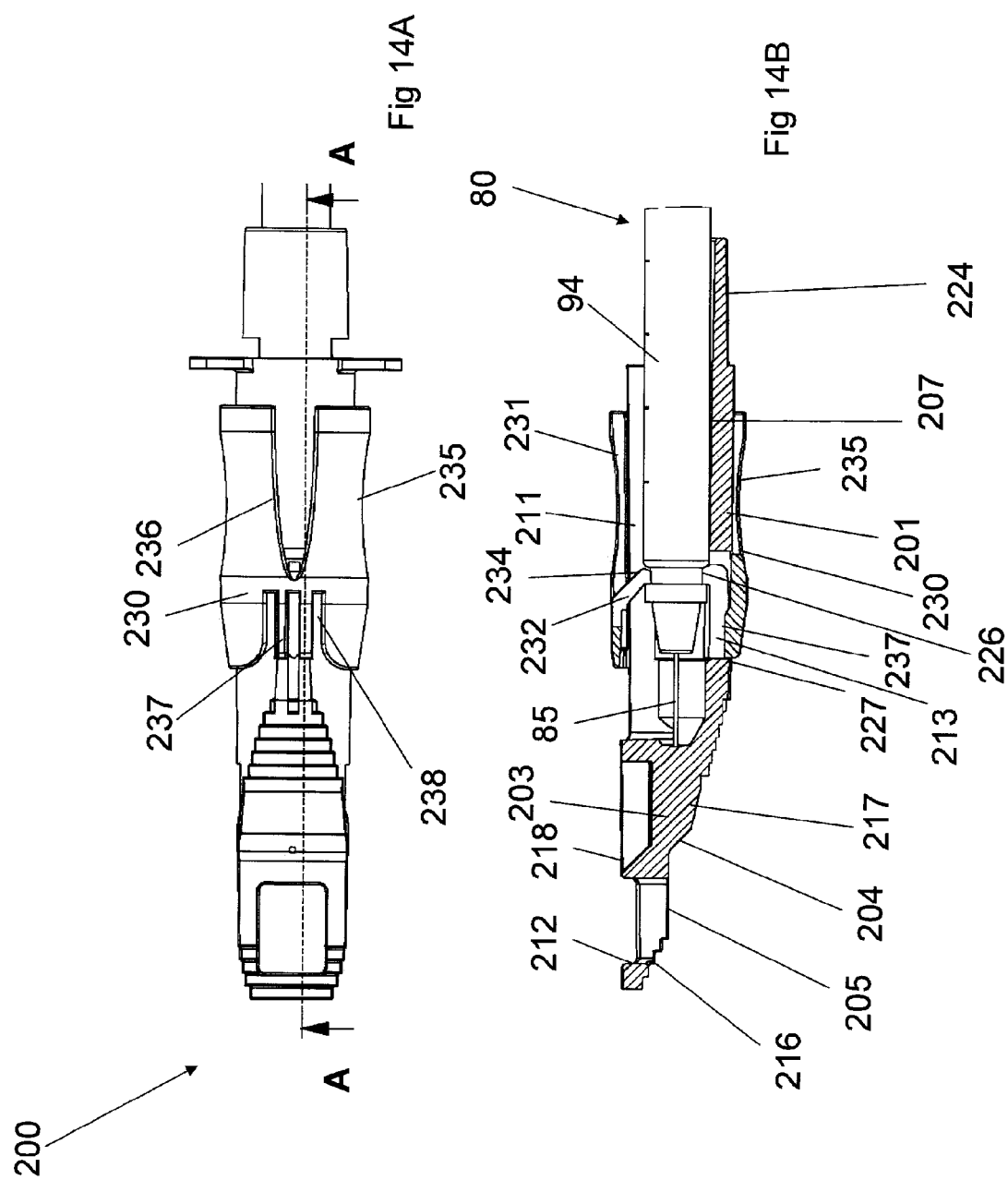

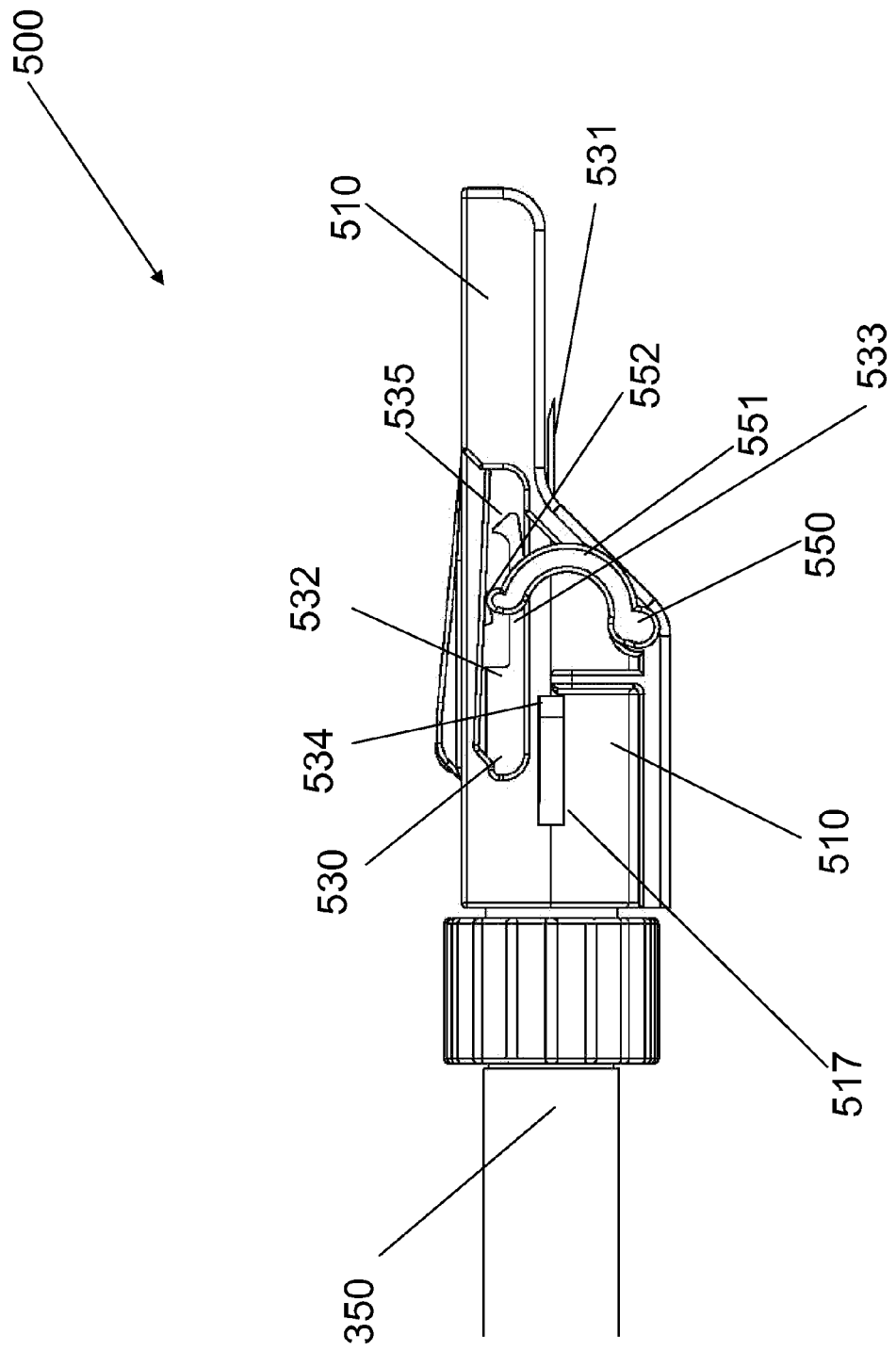

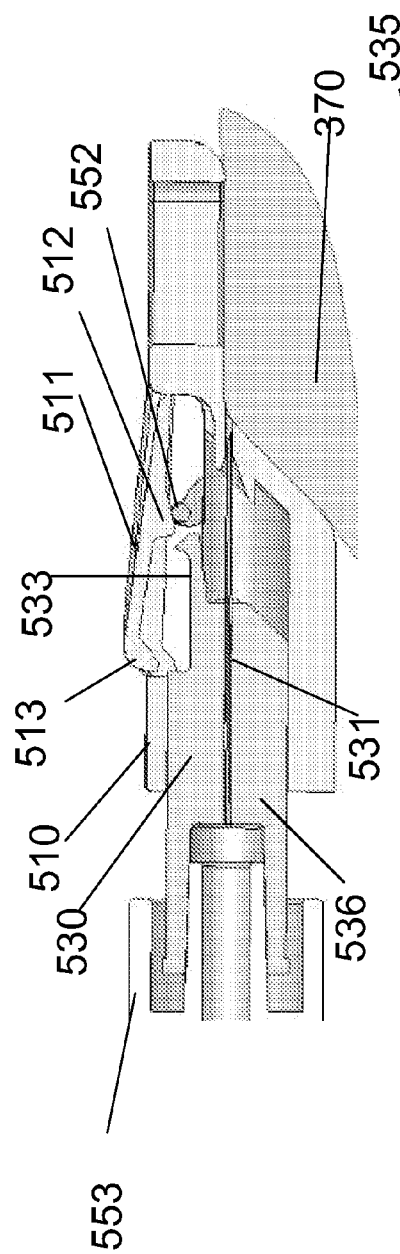
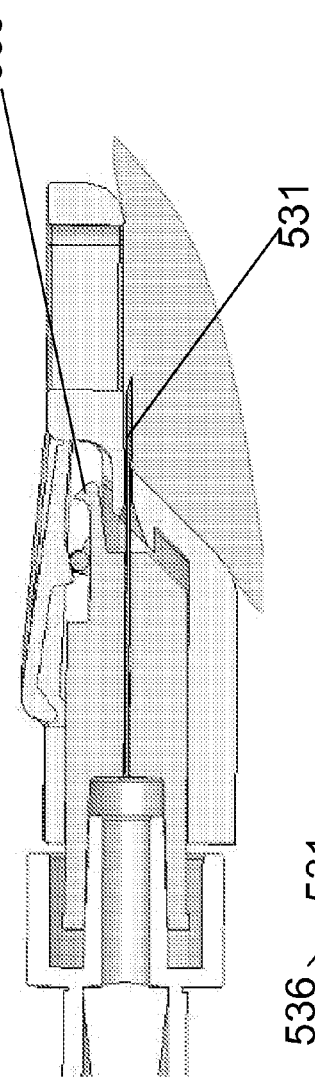
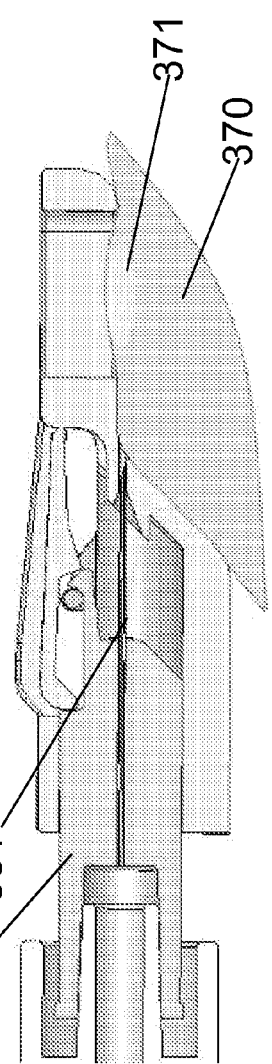
Fig 32A
Fig 32B
Fig 32C

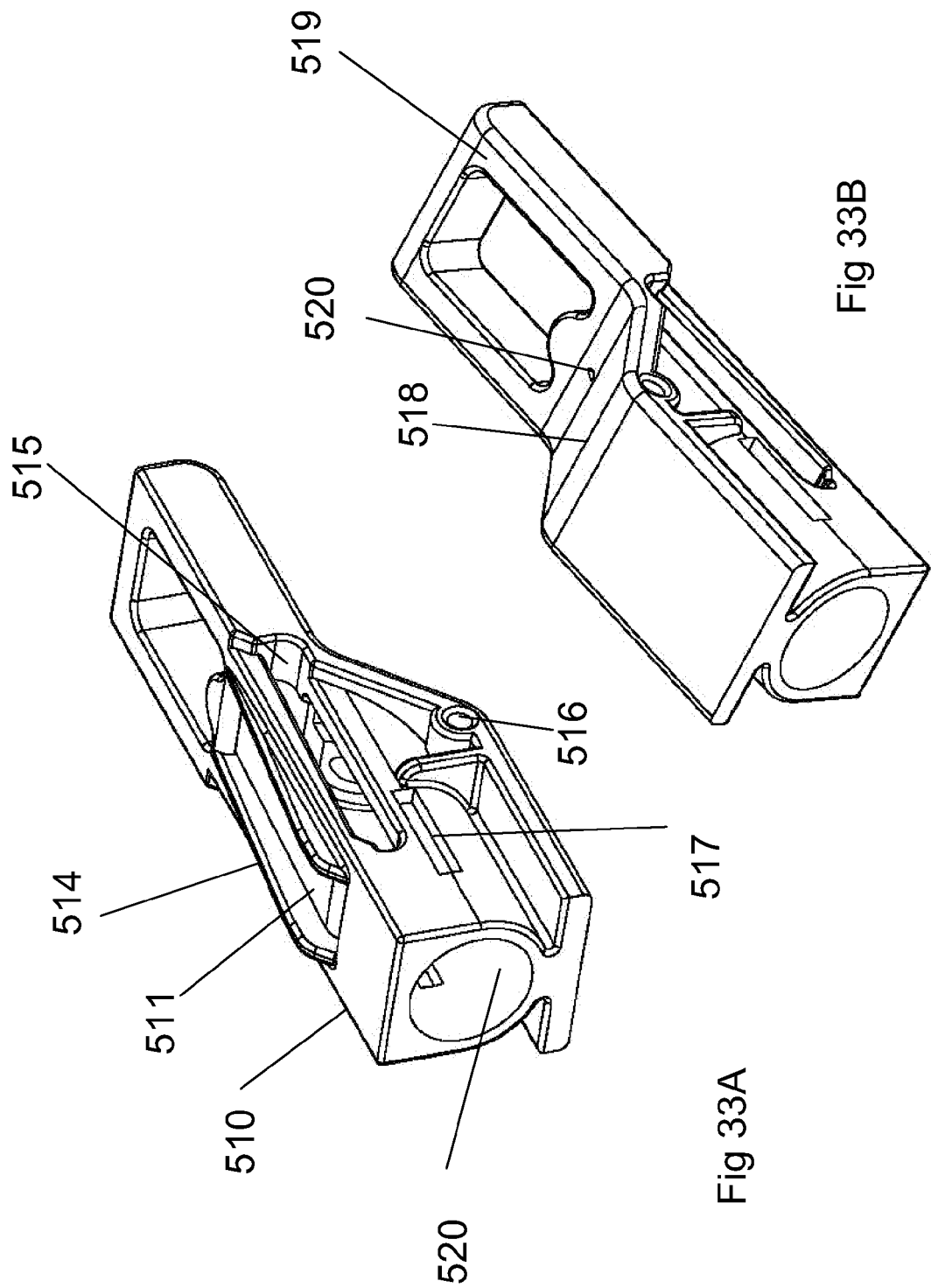

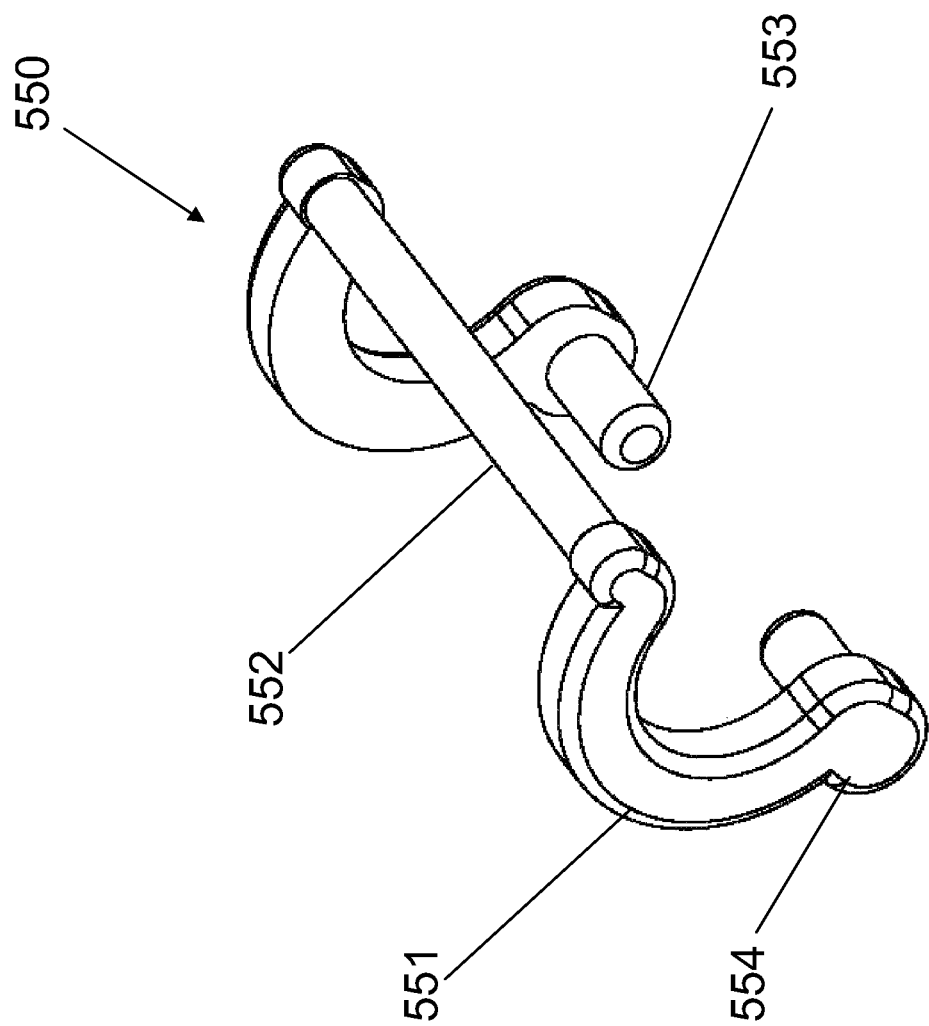

METHODS AND DEVICES FOR INTRADERMAL INJECTION

CROSS-REFERENCE TO RELATED APPLICATION

This application is a section 371 of International Application No. PCT/US2008/061331, filed Apr. 23, 2008, which was published in the English language on Oct. 30, 2008 under International Publication No. WO 2008/131440 A1, which claims the benefit of U.S. Provisional Patent Application No. 60/925,609, filed Apr. 23, 2007 and U.S. Provisional Patent Application No. 60/928,423, filed May 10, 2007, the disclosure of which is incorporated herein by reference.

FIELD OF THE INVENTION

The present invention relates to methods and devices for intradermal injection of drugs, vaccines and other compositions. Specifically, adapter devices and needle assemblies are described that are attachable to, or form a part of, a drug delivery system such as a syringe to facilitate intradermal injection.

BACKGROUND

Intradermal injections are used for delivering a variety of diagnostic and treatment compositions into a patient. Substances may be injected intradermally for diagnostic testing, such as to determine a patient's immunity status against tuberculosis and the status of allergic diseases. Vaccines, drugs and other compounds may also be delivered intradermally. In many instances, intradermal delivery is preferred because it generally requires a smaller volume dose of the diagnostic or treatment compound than other delivery techniques. An intradermal injection is made by delivering the substance into the epidermis and upper layer of the dermis. There is considerable variation in the skin thickness, both between individuals and within the same individual at different sites of the body. Generally the outer skin layer, or the epidermis, has a thickness between 500-200 microns and the dermis, the inner and thicker layer of the skin, has a thickness between 1.5-3.5 mm.

Making intradermal injections is difficult and generally requires an experienced nurse or medical professional. Incorrect placement of the tip of the needle cannula leads to a failed injection. The placement of the needle tip deeper than about 3.0 mm has the potential of delivering the injection into the subcutaneous region, where the intradermal dosage may be insufficient. Incorrect placement of the needle cannula may also puncture the skin again after being inserted into dermis, with the delivered compound being lost on the surface of the skin. Injection is often followed by a jet effect, with the compound exiting the injection site through the needle puncture track. The jet effect is even more pronounced for injections through a needle placed perpendicular to the injection site and in particular for shallow delivery. The success of intradermal injections is often determined by the experience of the healthcare professional. The preferred intradermal injection technique (using a standard needle) requires the healthcare professional to stretch the skin, orient the needle bevel to face upward, and insert a short bevel needle cannula at an angle of around 10-15 degrees, assuring that 2 to 3 mm of the needle cannula are located in the skin. The needle tip ends up positioned in the dermis or close to epidermis boundary. The compound is slowly injected into the skin of the patient, forming a blister or wheal. The insertion of the needle at an incorrect angle and/or depth results in a failed intradermal injection. Intradermal (ID) injection has been considered for immunization in the past, but has generally been rejected in favor of more reliable intramuscular or subcutaneous routes of administration because of the difficulty in making a successful ID injection.

Administration into the region of the intradermal space has been routinely used in the Mantoux tuberculin test, in which a purified protein derivative is injected at a shallow angle to the skin surface using a 27 or 30 gauge needle and a standard syringe. The technique is known to be quite difficult to perform and requires specialized training A degree of imprecision in the placement of the injection results in a significant number of false negative test results. As a result, the Mantoux approach has not led to the use of intradermal injection for systemic administration of substances, despite the advantage of requiring smaller doses of substances.

There have been attempts to develop devices that would assure a precise needle penetration depth during ID injection which tends to vary due to tissue compliance, penetration angle, skill level and other factors. These are detailed in U.S. Pat. Nos. 4,393,870 20 and 6,200,291 and US Published Patent Applications no. 2003/0093032, 2004/0147901. These devices employ complex constructions that tension the skin by vacuum, expanding the mounting surface prior to the needle insertion.

Alchas et al. developed a unique intradermal needle assembly for the delivery of compounds into the intradermal space by penetrating the dermis perpendicularly to its surface. A limiter supporting the needle is placed on the skin, the needle inserted, and the compound delivered. The penetration depth is in the 0.5 to 3 mm range, with a device limiter setting the penetration depth. There is a broad range of patents, issued and pending, defining different features of the system. U.S. Pat. Nos. 6,494,865, 6,569,123, 6,689,118, 6,776,776 and others, and U.S. Patent Publication no. 2003/0199822 describe such systems. The main limitation of the systems developed by Alchas et al. is the broad range of deposit depth due to assembly tolerances, needle bevel and the variations in skin properties. Another concern is back flow through the needle channel from the deposit pool to the surface of the skin due to a short direct channel formed by the needle. The jet effect further limits the performance when a shallow delivery is attempted.

Shielding and disposal of the contaminated needle cannula is a primary concern upon completion of an injection. It is preferable to cover the contaminated needle as soon as the intradermal injection is completed. A number of different approaches to shielding the contaminated needle are discussed in U.S. Pat. Nos. 4,631,057, 4,747,837, 4,801,295, 4,998,920, 5,053,018, 5,496,288, 5,893,845 and others.

The lack of suitable devices to accomplish reproducible delivery to the epidermal and dermal skin layers has limited the widespread use of the ID delivery route. Using conventional devices, ID injection is difficult to perform, unreliable and painful to the subject. There is thus a need for devices and methods that will enable efficient, accurate and reproducible delivery of agents to the intradermal layer of skin.

SUMMARY OF THE INVENTION

The present invention relates to devices and methods for the administration of compositions into the intradermal layer of the skin. An adapter device is provided, according to one aspect of the present invention, that facilitates intradermal delivery and can be used with minimal training Specifically, the adapter device minimizes the user skill required for correct insertion of the needle and accurate administration of an intradermal dosage.

In one embodiment, the adapter device of the present invention is intended for use with a conventional drug delivery system, such as a syringe, with the adapter and the syringe being arranged in a sliding relationship. Alternatively, a needle assembly may be provided integrally with the adapter device, eliminating the need for a needle integral with a syringe. In one embodiment of the adapter device, the user is able to observe the drug injection process. After the injection is completed, the user removes and discards the syringe and the adapter. In some embodiments, the user shields the needle by placing the adapter in a discard position following injection.

Adapter devices and needle assemblies of the present invention have surfaces that contact and deform the skin to provide an injection site at which the needle cannula can be inserted and then extended generally parallel to, but below, the surface of the skin. Adapter devices generally have first and second primary skin contacting surfaces provided on generally different, adjacent planes and positioned at an angle of less than 180° relative to each other, which act to deform a target tissue site when the adapter is applied to the skin. In use, the skin conforms to the first and second primary skin contacting surfaces of the adapter, and the needle cannula penetrates through the epidermis and dermis at a shallow angle to the surface of the skin, for example at an angle of 10° to 70°, preferably 15° to 6°. The cannula is further extended into the dermis along a path generally parallel to the second primary skin contacting surface for a distance, and the injectite is deposited in the dermal layer at a distance from the cannula penetration site. The adapter may include a first secondary skin contacting surface positioned proximal to the first primary skin contacting surface and/or a second secondary skin contacting surface positioned distal to the second primary skin contacting surface which act to limit tissue distortion.

The arrangement and configuration of the first and second primary skin contacting surfaces, and the angle at which the needle cannula exits the adapter device, facilitate extension of the cannula into the dermal layer at a depth, and for a distance, that allows deposition of the injected compound in the dermis and far enough away from the cannula penetration site to prevent loss of the injected composition. The structure of the adapter device provides a path for the cannula to enter the skin at a shallow angle to the surface of the skin, ensuring that the composition is delivered to the dermal layer rather than subcutaneously, and also limits the distance the cannula travels, ensuring that the composition is deposited in the dermal layer at an appropriate distance from the injection site.

The eventual placement of the needle tip closely follows the results of a well performed manual ID needle placement technique. The deformation of the skin and the underlying tissue during the application of the adapter and syringe assembly blocks the needle pathway to the surface of the skin after the assembly is removed. This technique resembles a Z-track approach used for intramuscular injections where the tissue layers are shifted prior to injection to minimize the backflow through the cannula channel after injection.

The positioning of the cannula tip in the dermis, and the length of the cannula extending into the dermis is controlled by the design and manufacture of the adapter. The cannula length in the dermis is selected to facilitate delivery to the dermis and to minimize the back flow and is generally set in the 0.25 mm to 8 mm range and, in some embodiments, the depth of the cannula orifice in the dermis may be as shallow as 0.25 mm or as deep as 3.00 mm. A shallow positioning is further facilitated by the opportunity to use fine gauge needles. The use of fine gauge cannulas is possible because minimal deflection forces act on the cannula during insertion and is also facilitated by the conventional lancet geometry minimizing the forces acting on the cannula and cannula deflection.

The cannula may be positioned at a slight angle to the second primary skin contacting surface in order to increase or decrease the orifice placement depth in the dermis while the cannula is being inserted. The cannula orifice placement depth can also be set by the curvature of the second primary skin contacting surface of the adapter.

Various features and advantages of this invention will become apparent to those skilled in the art from the following detailed description of the currently preferred embodiments.

BRIEF DESCRIPTION OF THE DRAWINGS

FIG. 13A is a bottom view of the device in FIG. 7 (from the skin side) during merger with the syringe;

FIG. 13B is a cross sectional view of the device in FIG. 13A along the surface AA;

FIG. 14A is a bottom view of the device in FIG. 13A with the needle permanently shielded by the ring in discard position;

FIG. 14B is a cross sectional view of the device in FIG. 14A along the surface AA;

FIG. 31 is a side view of the device in FIG. 29 with the cannula inserted into dermis;

FIG. 32A-C illustrate cross sectional views of the device of FIG. 29 as merged with a syringe (FIG. 32A), as applied to the skin with the cannula inserted into dermis (FIG. 32B), and after injection with the cannula withdrawn (FIG. 32C);

FIG. 33 illustrates a perspective view of an adapter of a device of FIG. 29 as viewed from the top (FIG. 33A) and the bottom (FIG. 33B) of the component; and FIG. 34 illustrates a perspective view of the dermis sensor of the device of FIG. 29.

DETAILED DESCRIPTION OF THE INVENTION

An adapter for an intradermal (ID) injection is intended for use with a syringe or another drug delivery system. One embodiment is shown in and described with reference to FIGS. 1-6. An alternative embodiment incorporating a safety system is described in FIGS. 7-14. As used herein, "proximal" refers to the assembly end positioned towards the user or the drug delivery device, while "distal" defines the opposite end of the assembly positioned towards the skin of the patient.

Figure 1:
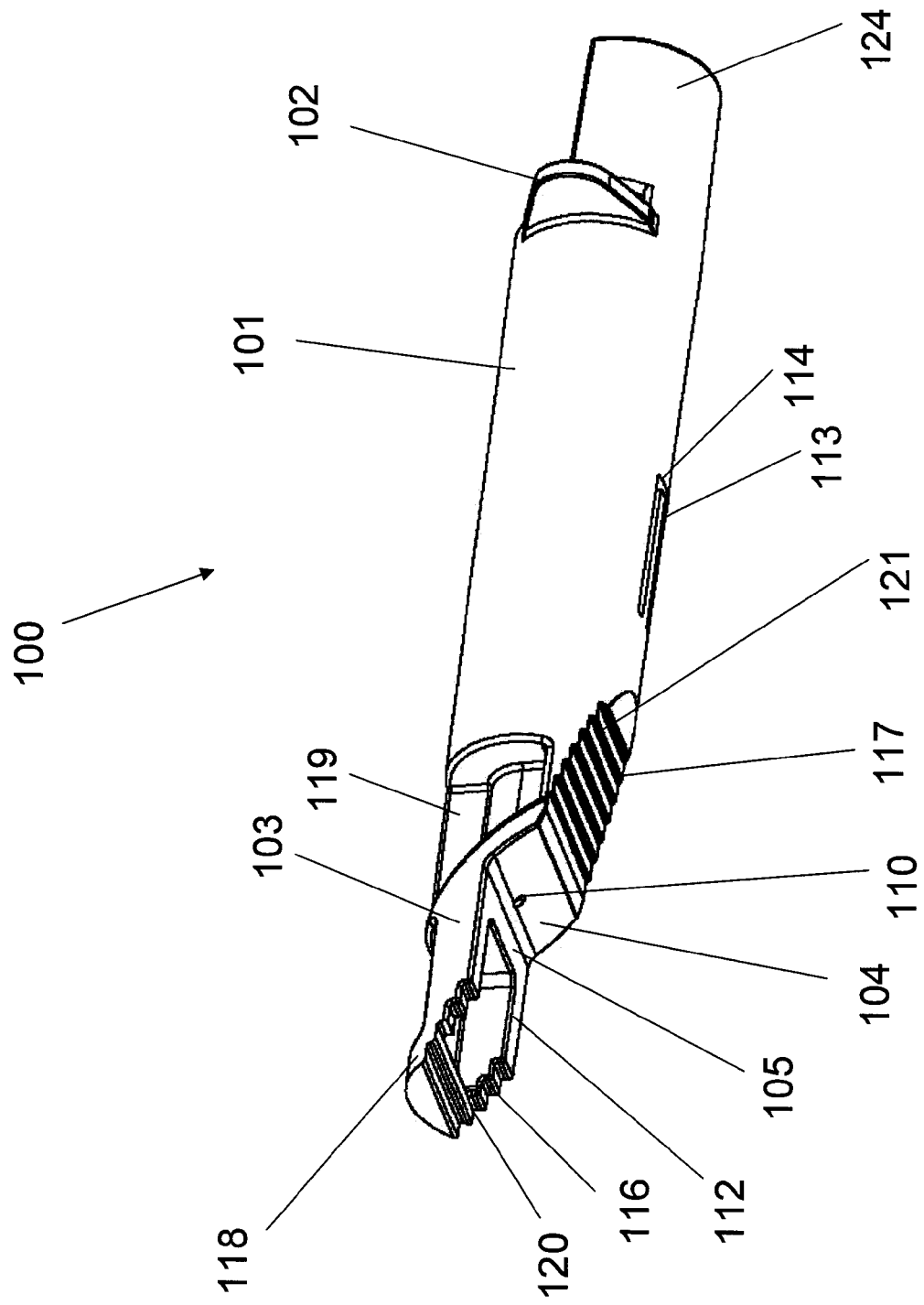
FIG. 1 is a side perspective view of one embodiment of an adapter according to the invention.

The external view of an adapter is illustrated in FIG. 1. The adapter 100 has a main body 101 and a distal section 103. The adapter main body 101 has finger grips 102 for ease of handling. The distal section of the adapter 103 has a first skin contacting surface 104 and a second skin contacting surface 105 positioned at an angle 123 relative to each other. Skin contacting surfaces 104 and 105 may be generally planar and connected to each other along one edge as shown in FIG. 1. Angle 123 is selected to allow for skin conformance to surfaces 104 and 105 when adapter 100 is applied to the dermis. Angle 123 is below 180° to allow for an adapter needle opening 110 to be positioned in the plane of skin contacting surface 104. In some embodiments, angle 123 is preferably less than about 165° and more than about 120°. This allows for penetration of the dermis by a needle of a drug delivery device upon the needle being forwarded through adapter needle opening 110. It also allows the needle to be advanced into the dermal space generally parallel to (e.g., at a shallow angle to) and below the skin surface. Skin contacting surfaces 104 and 105 may be arranged with an area of a gradual transition from surface to surface.

During use, skin contacting surface 105 is positioned on the surface of the skin above the site where the composition is deposited during injection and covers the bleb area formed when a compound is injected through the needle into the dermal space. To improve the skin visibility and to allow for skin distension, a skin observation window 112 may be provided in skin contacting surface 105.

Conformance of the dermis to the skin contacting surfaces 105 and 104 is improved when pressure is applied to an upper surface 118 of the adapter distal section 103. The conformance of the dermis to the skin contacting surfaces 104 and 105 may also be improved by minimizing deformation of the dermis and the underlying tissue. This can be achieved by providing a distal contact surface 116 and a proximal contact surface 117 of the adapter 100 arranged in proximity to the skin contacting surfaces 105 and 104, respectively, to minimize the tissue distortion during positioning of the adapter device on the skin and injection. Proximal contact surface 117 adjoins a proximal edge of first skin contacting surface 104 and may slope away from first skin contacting surface in a generally downwards direction with respect to needle opening 110 when the adapter is in the orientation shown in FIG. 1. Distal contact surface 116 adjoins a distal edge of second skin contacting surface 105 and may slope away from second skin contacting surface 105 in a generally opposite, upwards direction with respect to needle opening 110 when the adapter is in the orientation shown in FIG. 1. Tissue distortion may be reduced, desirably, when contact surfaces 116 and 117 are arranged in substantially similar planes.

Figure 2:
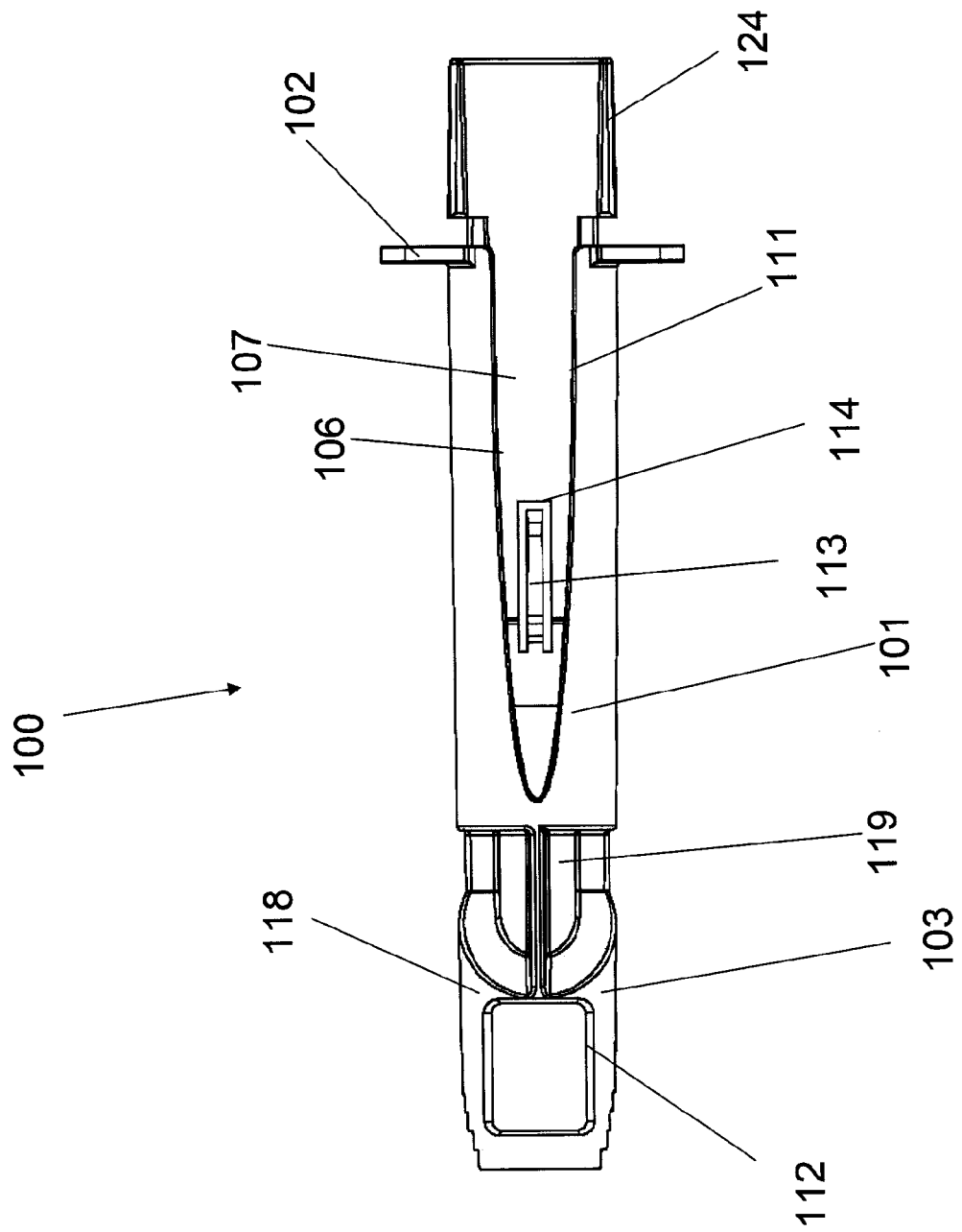
FIG. 2 is a top view of the device in FIG. 1.

Adapter 100 has an internal cavity 106 as illustrated in FIG. 2. Cavity 106 is arranged to accept a drug delivery device equipped with a cannula, such as a conventional syringe 50. Internal cavity 106 is arranged to accommodate syringe 50 in a sliding relationship. Syringe 50 slides on the internal adapter surface 107. Adapter body 101 is provided with an opening 111 allowing for the direct observation of merger of syringe 50 with adapter 100. An integral syringe support 124 is provided on adapter body 101 to guide syringe 50 during merger.

Figure 3:
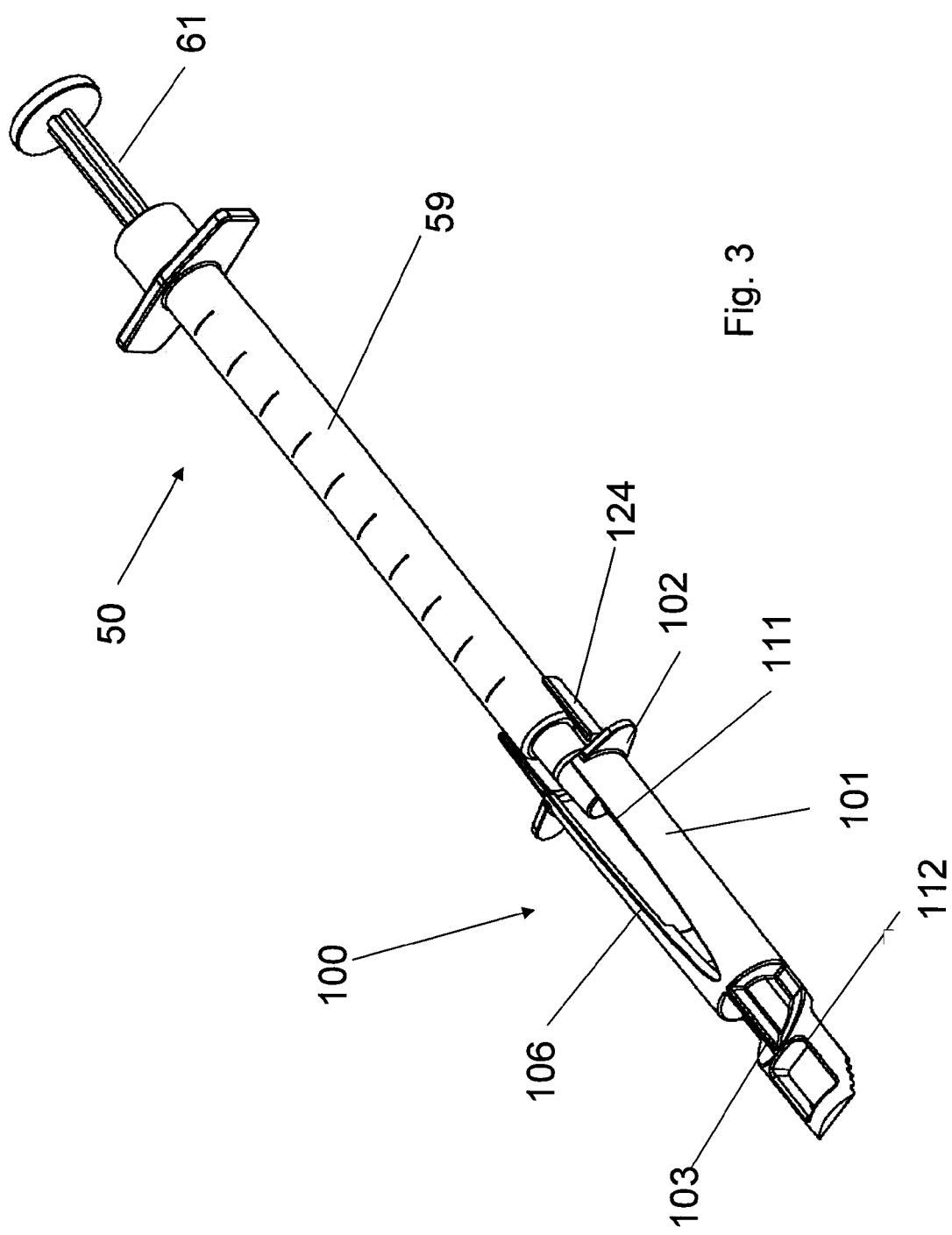
FIG. 3 is a top perspective view of the device in FIG. 1 during merger with a syringe.

Syringe 50 is placed into the adapter in a radial direction through opening 111 as illustrated in FIG. 3. The distal end of the syringe barrel 59 is placed on syringe support 124 which provides a guiding surface. Adapter opening 111 is formed to not interfere with the syringe cannula during the merger. The adapter body is provided with an integral latch 113. Latch 113 is separated from the body 101 by a slit 114 except for on its distal end where latch 113 is attached to the adapter body 101. Syringe 50 is pushed in a distal direction until a distal end 60 of the syringe barrel 59 contacts latch 113.

Figure 4:
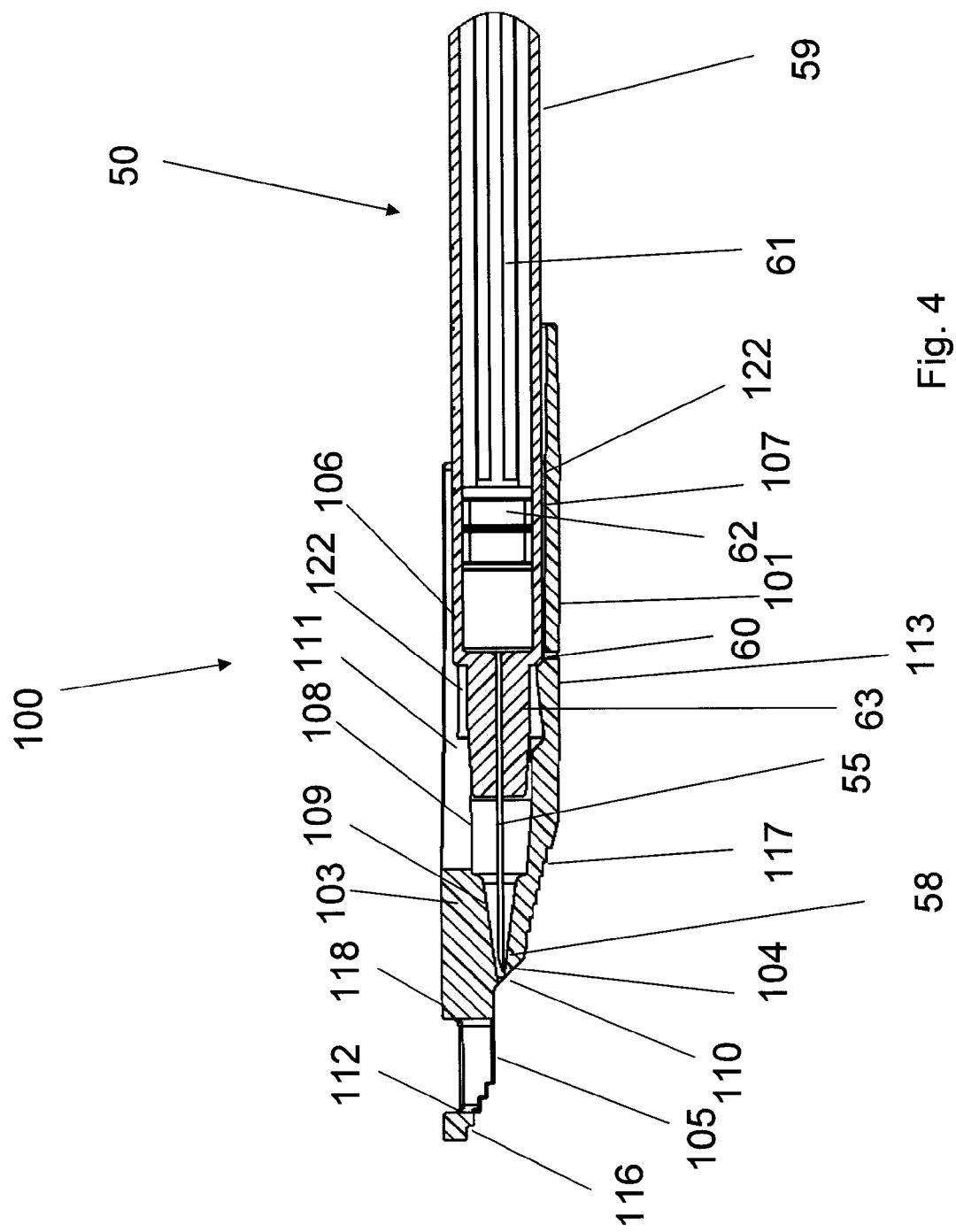
FIG. 4 is a cross sectional view of the device in FIG. 3 with the syringe placed further into the adapter in a pre-injection position.

The internal cavity 106 of the adapter has a cylindrical section 122 that accommodates syringe barrel 59, a reduced diameter section 108 that accommodates needle hub 63, and a needle opening cone section 109 that ends at first skin contacting surface 104 and adapter needle opening 110. The needle cannula 55 has a forward tip 58 with a bevel. The adapter is sized such that cannula 55 is enclosed in the adapter 100 when distal end 60 of syringe barrel 59 contacts adapter latch 113 as illustrated in FIG. 4.

Figure 5:
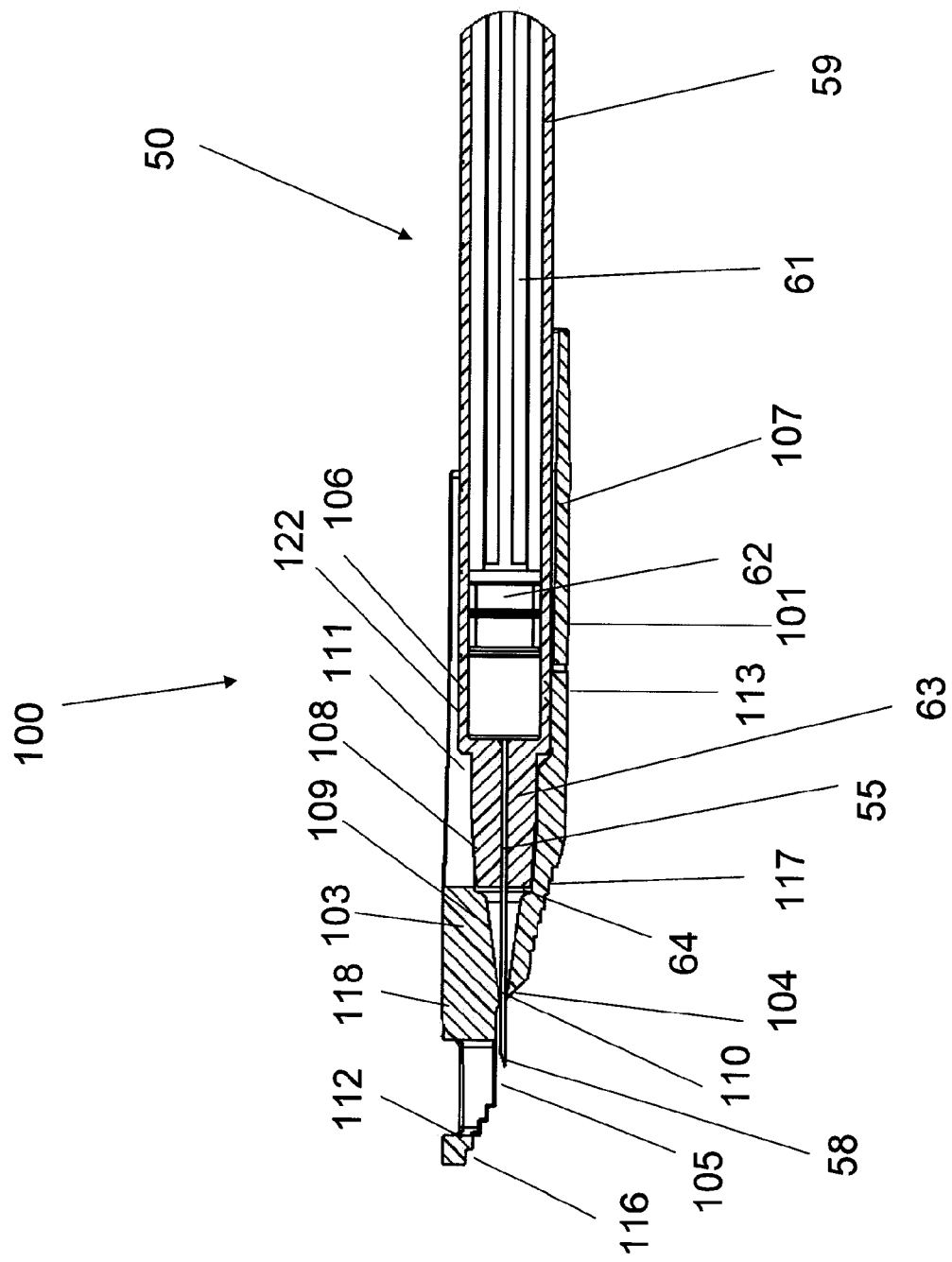
FIG. 5 is a cross sectional view of the device in FIG. 4 after extension of the needle into dermis and prior to compound injection.

In use, adapter 100 is applied to and held in contact with the dermis, as detailed below. An axial force is then applied to syringe barrel 59 causing the latch 113 to deflect when acted upon by the distal end 60 of barrel 59. The barrel 59 moves forward after the latch 113 is deflected. Cannula 55 then extends through needle opening 110 and is inserted into the dermis parallel to the skin surface. The needle insertion stops when a distal end 64 of needle hub 63 contacts the adapter 100 as shown in FIG. 5.

Figure 5A:
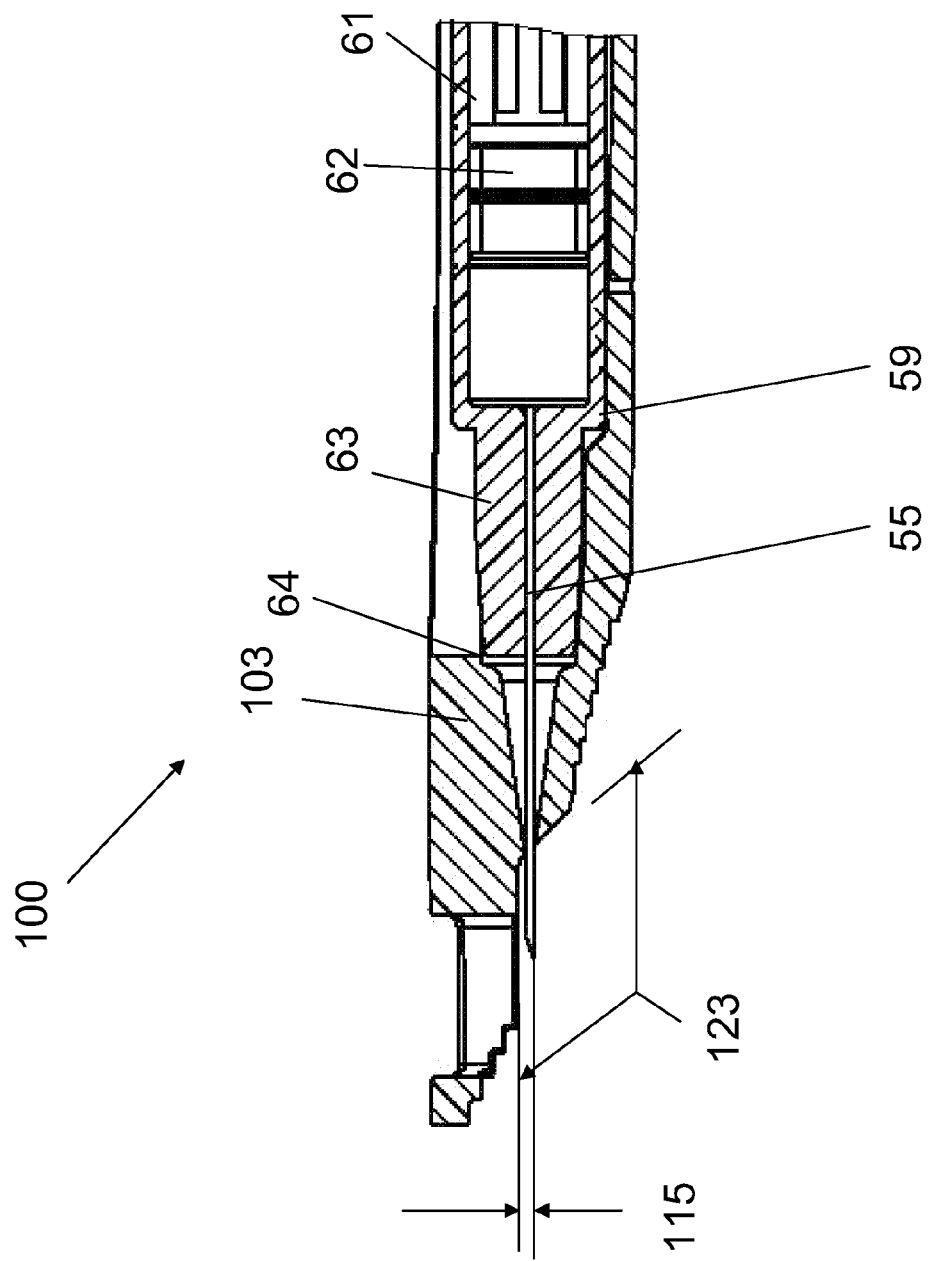
FIG. 5A is an enlarged view of the device and injection shown in FIG. 5.

FIG. 5A illustrates details of the adapter design. The first 104 and second 105 skin contacting surfaces are positioned at a relative angle 123. The angle allows for tissue deformation and for bringing the dermis into contact with these adapter primary surfaces. The position of needle opening 110 and the cannula orientation in the adapter are selected to result in cannula 55 being inserted parallel to the dermis surface at a desired depth 115 from the cannula center line.

The compound is expelled from the drug delivery device into the dermis by pushing on syringe rod 61 and advancing the stopper 62. The injection may be performed while the adapter is applied to the skin with some pressure. Alternatively, the pressure on the adapter towards the skin may be reduced during injection allowing for more dermis distention and welt formation. In another technique, the adapter may be somewhat elevated above the skin while maintaining the needle tip position in the dermis, in order to further improve the dermis distension.

Cannula 55 may be extracted from the skin and the cannula and syringe discarded while the adapter 100 remains in contact with the dermis. Alternatively, the adapter 100 may be removed from the skin together with the syringe and subsequently discarded.

Adapter finger contact surface 118 may be shaped to provide an indication to the user of where to apply pressure on contact surface 118 during insertion of cannula 55 into the dermal space. Adapter 100 may also be provided with a recess 119 to minimize the plastic volume of the device.

Figure 6:
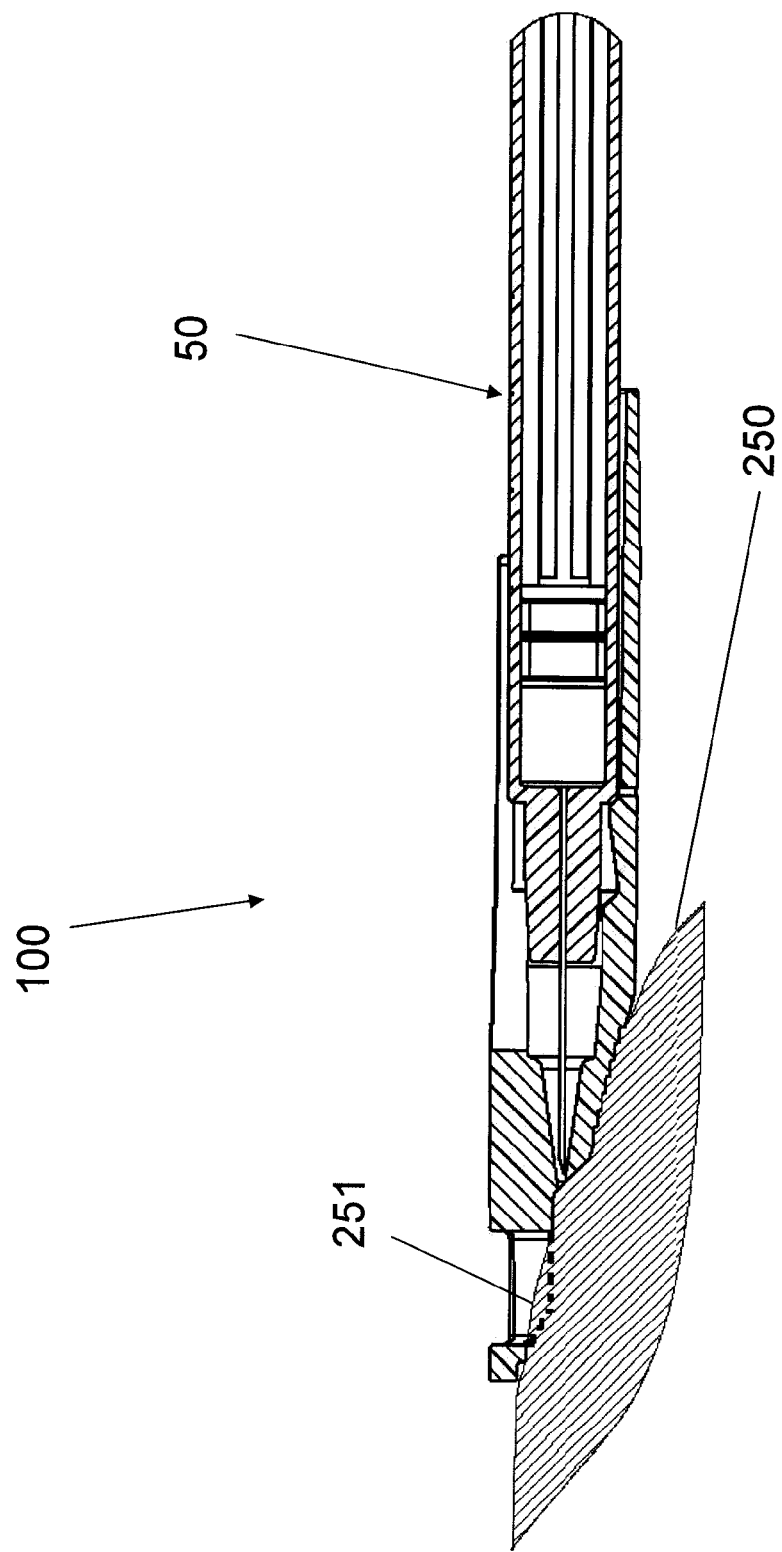
FIG. 6 is a cross sectional view of the device in FIG. 4 placed on a skin surface and illustrating the bulging of the dermis into the skin observation opening.

The skin tends to form a slight bulge 251 and protrude into observation opening 112 when the adapter is pushed toward the dermis 250 as illustrated in FIG. 6. The adapter may have an adapter body extension that extends into the opening 112. This extension, which would be positioned above the cannula 55, would support the dermis and prevent bulging of the skin thereby maintaining the desired depth of the needle forward tip during needle insertion. The skin will further bulge and protrude into the window during injection as a result of the bleb formation.

It is desirable to minimize distortion of the dermis and the underlying tissue during ID injection. This is accomplished through the design of the primary first and second skin contacting surfaces 104 and 105 and the secondary distal 116 and proximal 117 contact surfaces of the adapter. The orientation of secondary distal and proximal contact surfaces 116 and 117 is selected to form a surface with minimal distortions when considered together with the first skin contacting surface 104 and the second skin contacting surface 105.

It is also desirable to have a taut skin area in contact with the adapter to minimize the bulging of the skin into the observation opening 112. Areas of the skin contacting surfaces could have properties assisting in increasing adherence toward skin when the adapter is applied, such as sticky or rubbery surfaces. The skin contacting surfaces may be substantially flat, or they may be grooved or ridged, or they may be curved or provided in another configuration. The part of the adapter skin contacting surfaces 104 and 105 in the plane of the needle may be elevated compared to peripheral sections of the skin contacting surfaces. The resulting protruding parts of the contact surfaces in the plane of the cannula contact the skin during the initial phase of the adapter application resulting in a taut skin.

The distal 116 and the proximal 117 contact surfaces may be provided as extensions of the primary first and second skin contacting surfaces, and they may be equipped with ridges 120 and 121. The distal contact surface 116 may be placed into contact with the dermis first, allowing for skin tensioning. Subsequently, the second contact surface 117 may be brought into contact with the dermis, allowing the retention of the skin tensioning during the injection process.

In another embodiment, an adapter for an intradermal (ID) injection is equipped with a safety feature. This embodiment, which is also intended for use with a syringe or any other drug delivery system is illustrated in FIGS. 7-14.

Figure 7:
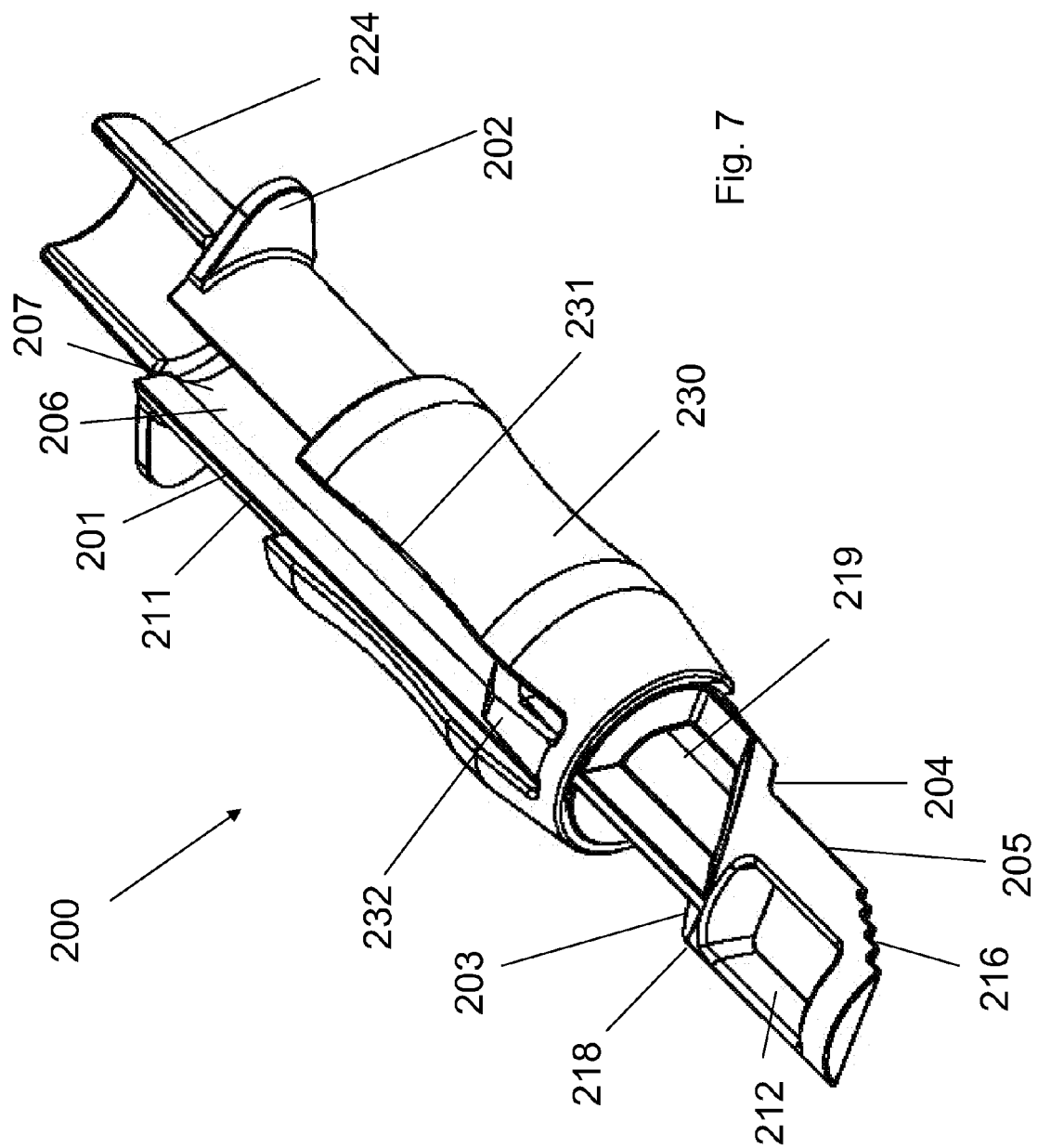
FIG. 7 is a top perspective view of another embodiment of an adapter according to the invention, having a safety ring.

An external view of the device is illustrated in FIG. 7. Adapter assembly 200 has an adapter body 201 and a safety ring 230. The features of adapter body 200 are similar to those of the adapter illustrated in FIGS. 1-6. The adapter body 201 has finger grips 202 for ease of handling and a syringe support 224. The adapter is also equipped with a delivery device opening 211 simplifying the adapter and syringe merger.

The distal section of the adapter 203 has two skin contacting surfaces 204 and 205 positioned at an angle 223 relative to each other similar to the adapter discussed above and illustrated in FIGS. 1-6. Angle 223, which has to be below 180 degrees to allow for the adapter needle opening 210 to be positioned in the plane of the skin contact surface 204 is selected to allow for skin conformance to these surfaces when the adapter is applied to the dermis. This arrangement allows for the penetration of the dermis by the needle of a drug delivery device upon the needle being forwarded through the needle opening 210. It also allows the needle to be advanced into the dermal space parallel to the skin surface and the adapter plane 205. The primary skin contacting surfaces 204 and 205 may be arranged with an area of a gradual transition from surface to surface. The adapter contact surface 205 covers the bleb area formed when the compound is injected. To improve the skin visibility and to allow for the skin distension a skin observation window 212 can be formed in the contact surface 205 of the adapter body distal section 203.

Conformance of the dermis to the adapter surface is improved when pressure is applied to the surface 218 of the adapter distal section 203. Conformance of the dermis to the adapter surfaces 204 and 205 is also improved by minimizing deformation of the dermis and the underlying tissue during application of the adapter to the skin This is achieved by the introduction of distal 216 and proximal 217 contact surfaces designed to minimize the tissue distortion during injection.

Figure 8:
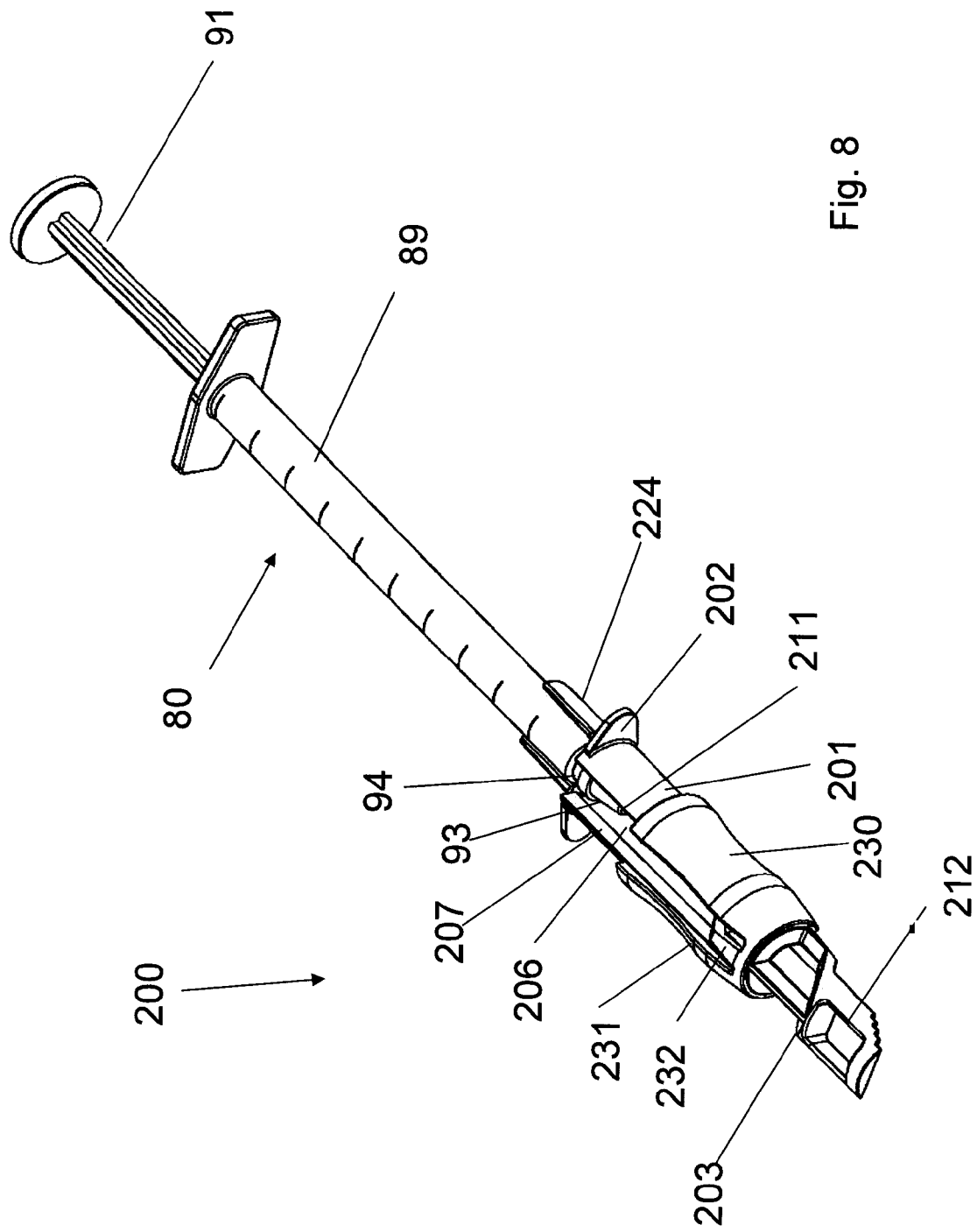
FIG. 8 is a top perspective view of the device in FIG. 7 during merger with a syringe.

The adapter 200 has an internal cavity 206 as illustrated in FIGS. 7 and 8. This cavity is arranged to accept a drug delivery device equipped with a cannula. FIGS. 7-14 illustrate a safety adapter intended for use with a conventional syringe 80 provided with an undercut 94 (such as, for example, Terumo SurGuard safety insulin or allergy syringes).

The adapter 200 has a safety ring 230 in a sliding relationship with adapter body 201. The ring 230 is initially in a most distal position as illustrated in FIGS. 7-10. Ring 230 has an observation window 231 coinciding with the window of the adapter body 211, and a latch 232. Latch 232 has a protrusion 233 for engaging the syringe. Ring 230 also has an undercut 234 in the latch area that retains ring 230 in the most distal position during the initial steps of the operation.

The internal cavity 206 of the adapter 200 is arranged to accommodate a syringe 80 in a sliding relationship. Syringe 80 slides on the internal surface 207 of the adapter body 201. The adapter body 201 is provided with an opening 211 that facilitates the merger of the adapter with syringe 80 by allowing the cannula passage and observation of the merger process. Adapter body 201 also has an integral syringe support 224 to simplify the adapter 200 and the syringe 80 merger by the user.

Figure 9:
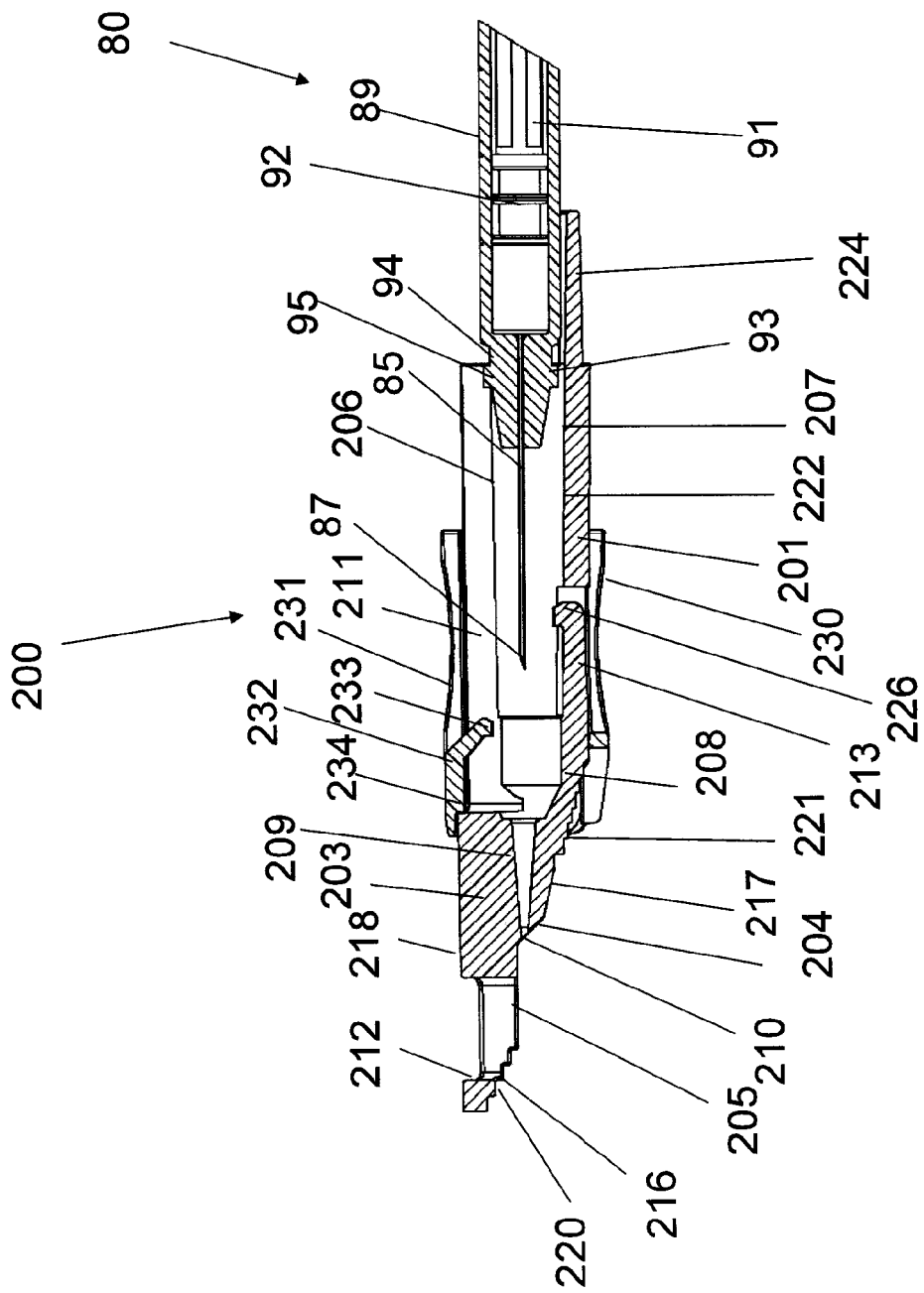
FIG. 9 is a cross sectional view of the device in FIG. 8.

The syringe 80 is placed into the adapter 200 through the adapter body opening 211 as illustrated in FIGS. 8 and 9. The distal end of the syringe barrel 89 is placed on the syringe support 224 which provides a guiding surface for further insertion. The adapter opening 211 does not interfere with the syringe cannula during the merger step.

Figure 10:
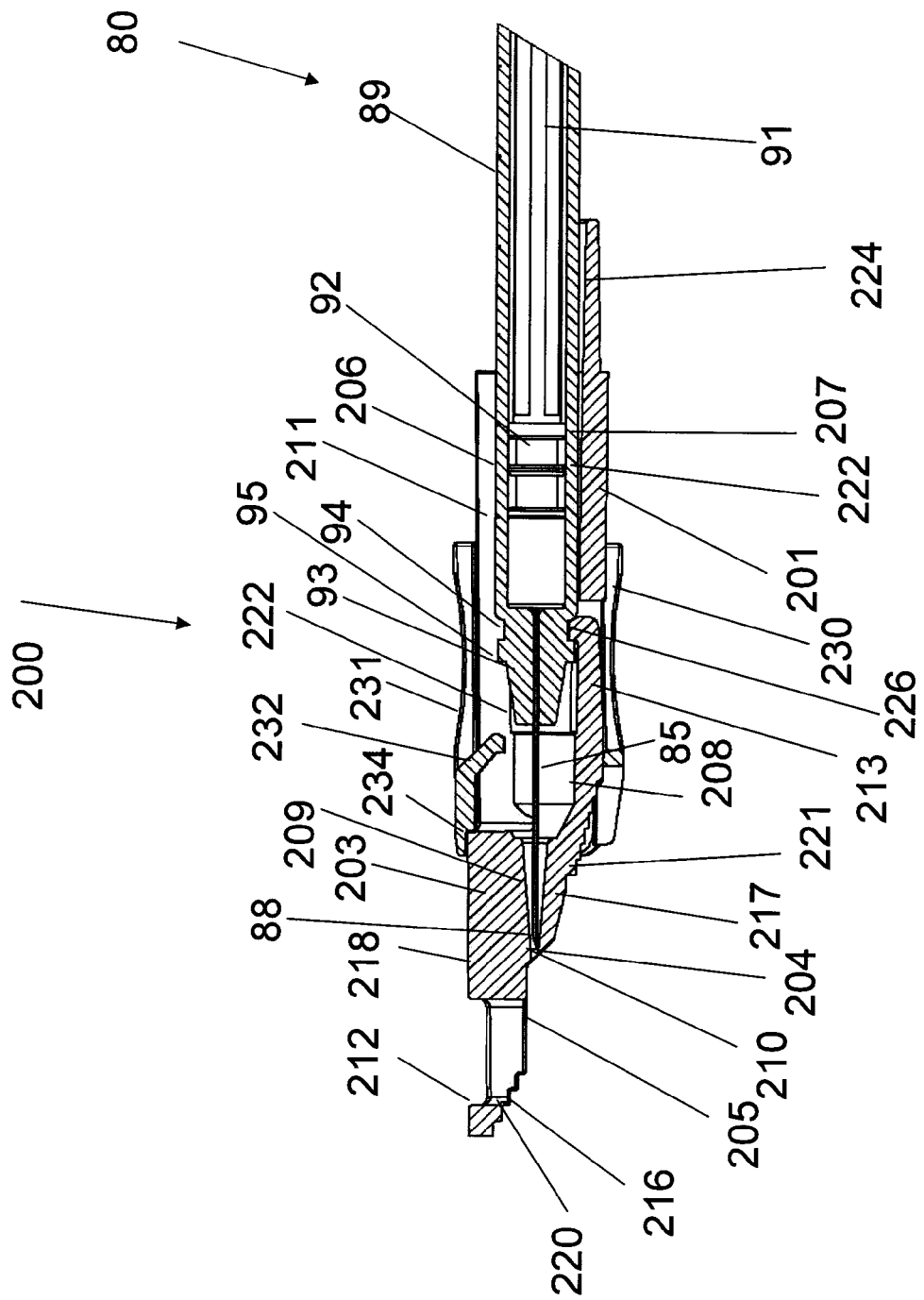
FIG. 10 is a cross sectional view of the device in FIG. 9 with the cannula in a pre-insertion position in the adapter prior to insertion into dermis.

The adapter body 201 has an integral latch 213, which is separated from body 201 by a slit 214 except for at its distal end where the latch is attached to the adapter body 201. The syringe is pushed in a distal direction until the distal end of the syringe hub leading edge 95 contacts the latch protrusion 226 and deflects the latch 213 with the protrusion 226 jumping into the undercut 94 of the syringe needle hub 93 as illustrated in FIG. 10. The internal adapter cavity 206 has a cylindrical section 222 that accommodates the syringe barrel 89, a reduced diameter section 208 that accommodates the needle hub 93, and a needle opening cone section 209 ending at adapter needle opening 210.

Needle cannula 85 has a forward tip 88 with a bevel. The cannula 85 is held within the adapter 200 when the syringe barrel 89 contacts and engages the adapter latch 213 as illustrated in FIG. 10.

Figure 11:
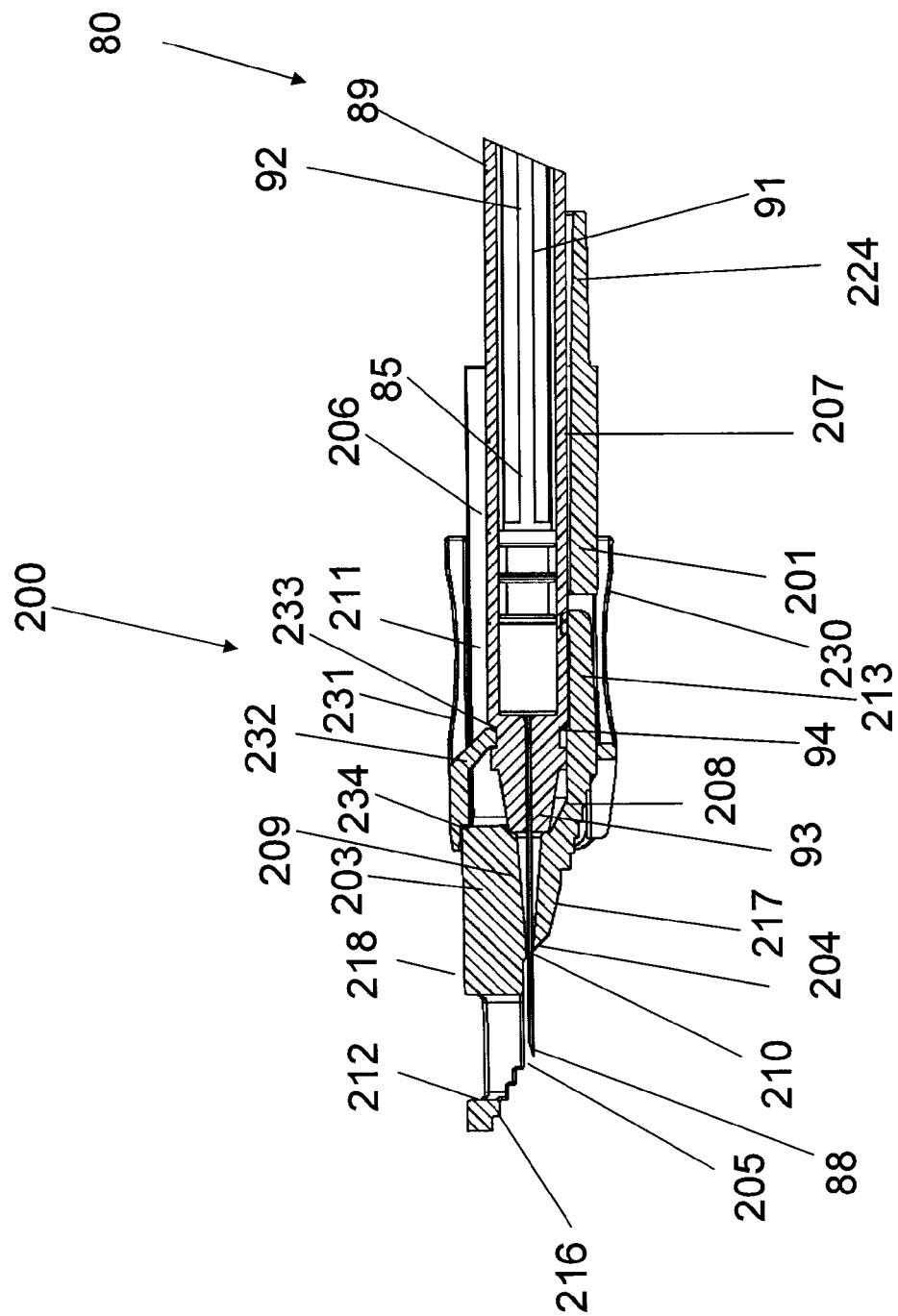
FIG. 11 is a cross sectional view of the device in FIG. 10 after cannula extension and insertion into dermis and prior to compound injection.

In use, the adapter 200 is applied to and held in contact with the dermis. An axial force is applied to the syringe barrel 89 causing the adapter latch 213 to deflect when acted upon by the barrel distal end 96, thereby enabling barrel 89 to move forward. The cannula 85 penetrates the skin through the needle opening 210 and is automatically inserted into the dermis parallel to the skin surface in contact with the second primary surface 205 for a preset cannula shaft length. The needle insertion stops when the distal end 95 of the syringe hub 93 contacts adapter body 201 as illustrated in FIG. 11.

Prior to the needle hub leading edge 95 contacting the adapter body, the ring latch 232 contacts the needle hub and gets deflected. The latch protrusion 233 simultaneously engages the syringe with the distal motion of the syringe being stopped by contact of the needle hub with the adapter body 201.

The details of the adapter 100 design illustrated in FIG. 5A are applicable to the safety adapter 200. The syringe needle penetrates adapter first contact surface 204 and is further inserted parallel to the second contact surface 205. The relative angle between the first and second surface allows tissue deformation, bringing the dermis in contact with the adapter. The position of the needle opening 210 and the cannula orientation in the adapter are selected to result in the needle being inserted parallel to the dermis surface at a desired depth from the cannula center line.

The compound is expelled from the drug delivery device into the dermis by pushing on the syringe rod 91 and advancing the stopper 92. The injection may take place while the adapter is applied to the skin with some pressure. Alternatively, the pressure on the adapter toward the skin may be reduced allowing for more dermis distention and bleb formation. In another technique, the adapter may be somewhat elevated above the skin while maintaining the needle tip position in the dermis, thereby further improving the dermis distension.

Figure 12:
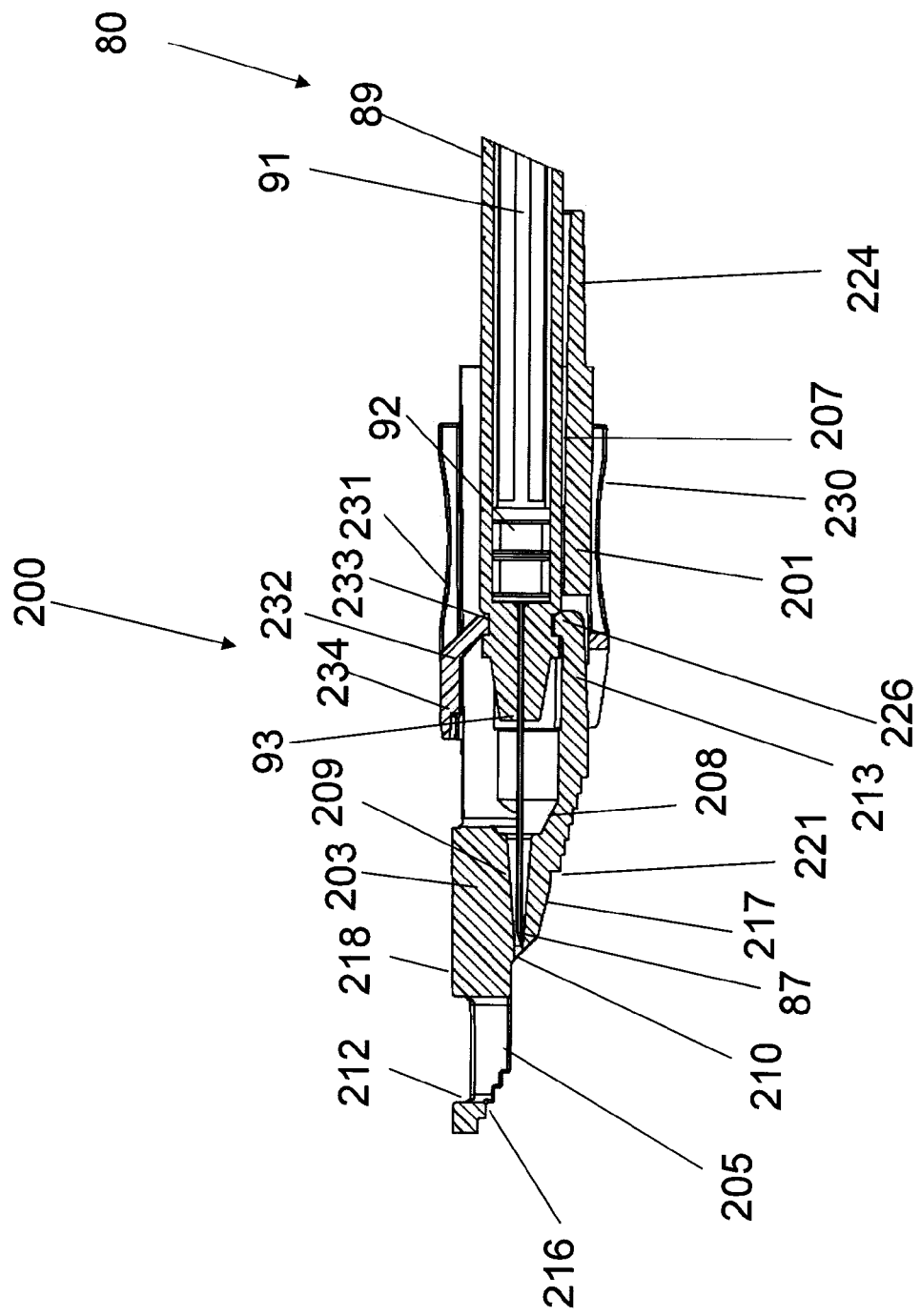
FIG. 12 is a cross sectional view of the device in FIG. 11 after the cannula is withdrawn from the dermis and shielded.

After injection, the syringe cannula 85 is extracted from the skin by removing the adapter and the syringe from the site. At this point the adapter safety ring 230 and the syringe 80 are engaged. The cannula is than permanently shielded by pulling the barrel in respect to the adapter or by pulling the safety ring toward the finger grips 202. The discard position of the adapter 200 engages with the syringe 80 as illustrated in FIG. 12. The needle forward tip 88 is thus permanently hidden in the adapter body 201.

The adapter 200 latches retain the cannula in the discard position as illustrated in FIGS. 12 and 13. The safety ring 230 has a bottom opening which allows for unobstructed deflection of the adapter latch 213 during operation. The safety ring is further equipped with two discard latches 337 separated from the safety ring 230 by a slit 238.

The adapter finger contact surface 218 may be shaped to provide an indication to the user as to where to apply pressure on the surface during needle insertion into the dermal space. For example, the surface may be curved to match the finger tip profile and have a different texture from the rest of the adapter. The adapter 200 may also have a recess 219 to minimize the plastic volume as illustrated in FIG. 7.

It is desirable to minimize the distortion of the dermis and the underlying tissue during ID injection. This goal is accomplished by the distal 216 and the proximal 217 contact surfaces of the adapter. The orientation of contact surfaces 216 and 217 is selected to form a surface causing minimal distortions of the dermis when considered together with the first skin contacting surface 204 and the second skin contacting surface 205.

It is also desirable to have a taut skin area in contact with the adapter to minimize bulging of the skin into the opening 212. Areas of the skin contacting surfaces may have properties assisting in increasing adherence toward skin when the adapter is applied, and the contacting surfaces could be substantially curved as discussed above. The part of the adapter contacting surfaces in the plane of, and in proximity to the needle may be elevated compared to the peripheral sections of the skin contacting surfaces. The protruding peripheral parts of the contact surfaces would contact the skin during the initial phase of the adapter application resulting in a taut skin.

The secondary distal 216 and proximal 217 skin contacting surfaces of the adapter may be equipped with ridges 220 and 221 or other surface protrusions. The rigged distal contact surface 216 may be placed into contact with the dermis first, allowing for skin tensioning. Subsequently the second contact surface 217 is brought into contact with the dermis allowing for the skin tension to be retained during the insertion process.

Figure 15:
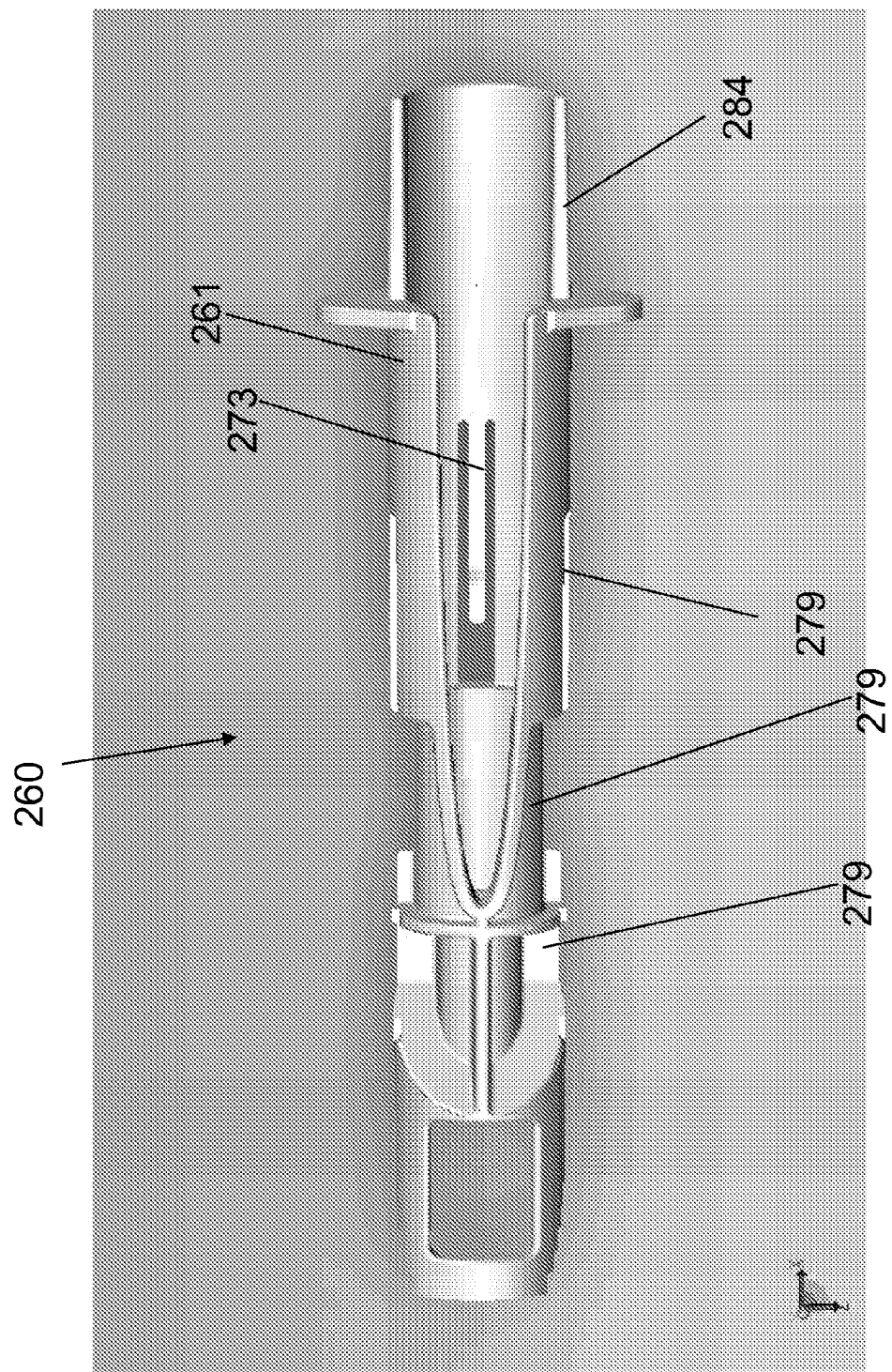
FIG. 15 is a top view of yet another embodiment of an ID adapter having an alternative latch, syringe support and wall thickness implementation.
Figure 16:
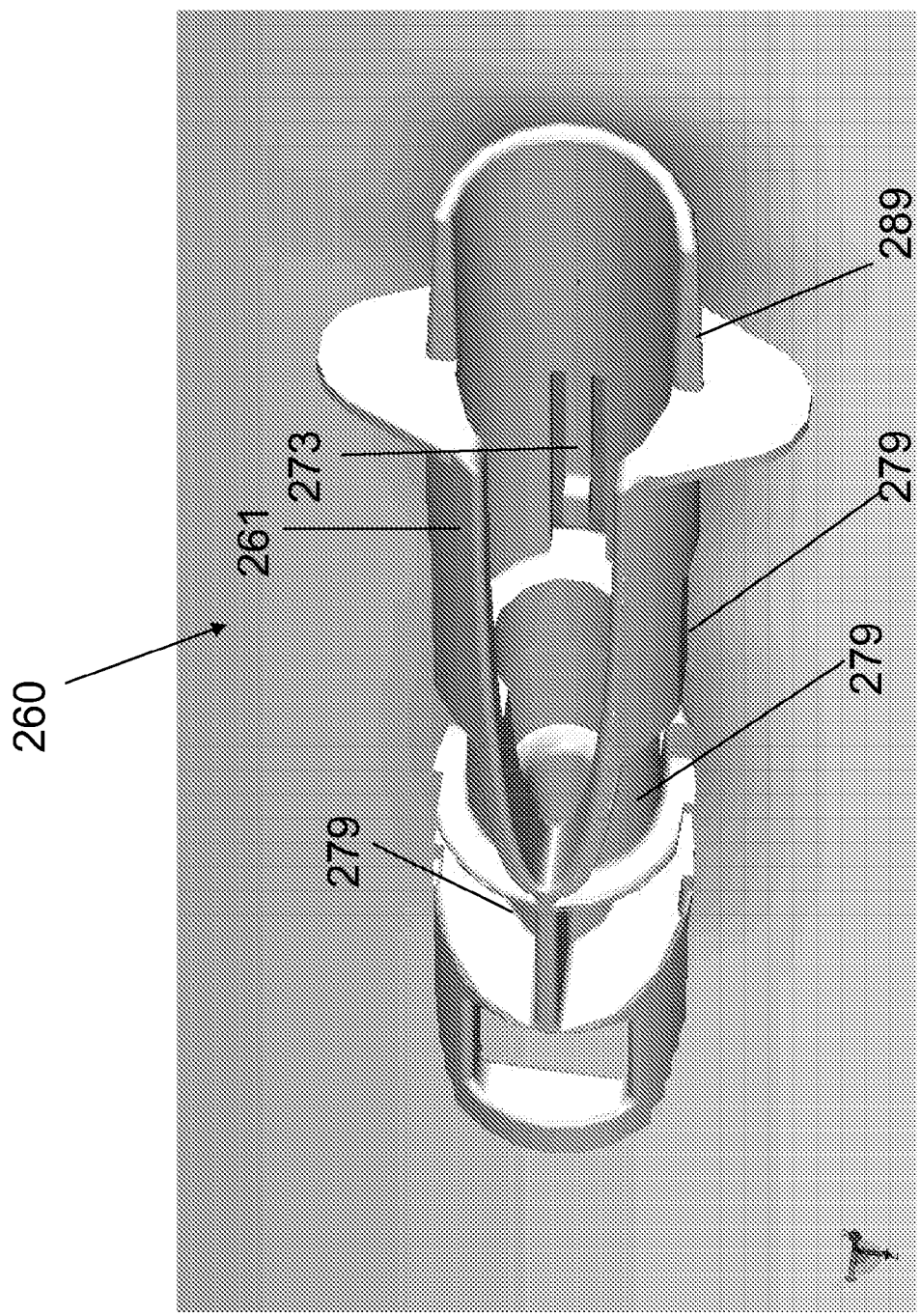
FIG. 16 is another perspective view of the ID adapter of FIG. 15.

The ID adapter illustrated in FIGS. 1-6 may be modified, for example, as shown in FIGS. 15 and 16, to improve manufacturability of the ID adapter. ID adapter 260 has the same essential features as the ID adapter illustrated in FIGS. 1-6 and has a reduced wall thickness in the area of recesses 279. Syringe support 284 was formed as a direct extension of the adapter body 261. In this embodiment of ID adapter 260, latch 273 protrudes from the proximal surface of the body 261, providing improved manufacturability.

Alternative needle assemblies for intradermal (ID) injection employing the ID adapter and intended for use with a syringe or any other drug delivery system are illustrated in FIGS. 17-34 with a first embodiment being shown in FIGS. 17 through 23; a second embodiment being shown in FIGS. 24 through 28; and a third embodiment being shown in FIGS.

29 through 34. The adapter geometry features are detailed for the first preferred embodiment but are implemented in all three embodiments.

Figure 17:
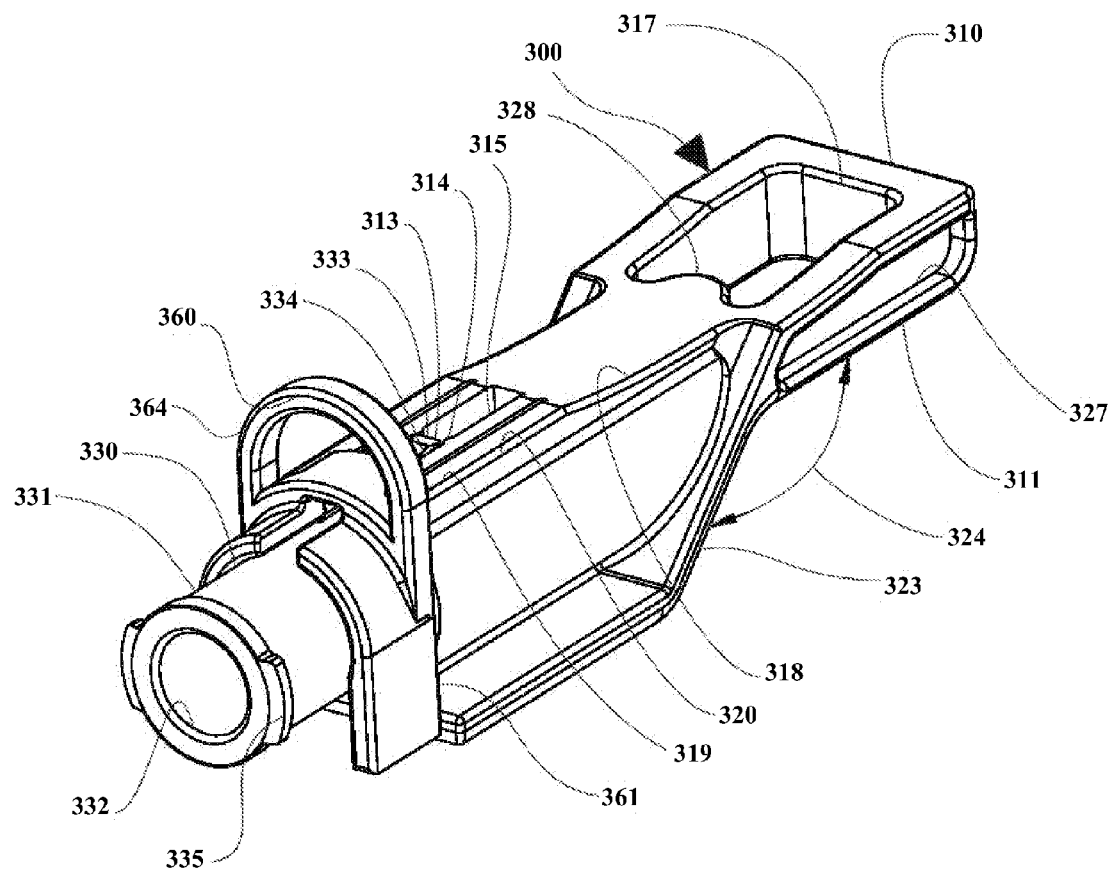
FIG. 17 is a side perspective view of an ID needle assembly according to the invention as stored.

A side perspective view of the first preferred embodiment of the device is illustrated in FIG. 17. The main components include an adapter 310, a needle cannula assembly 330 and a safety clip 360. The adapter 310 is in a sliding relationship with the needle cannula assembly 330 and partially surrounds it. The safety clip 360 retains the relative position of the adapter 310 to the needle cannula assembly 330 during storage and during the attachment to a drug delivery device.

The needle cannula assembly 330 has a hub portion 331 to connect to a syringe 350 or another drug delivery device as illustrated in FIG. 18. The hub portion 331 could have a female luer 332. In designs employing a luer lock the hub portion would have luer lock wings 335. FIGS. 18 through 22 do not illustrate the thread of the syringe luer lock design.

The adapter 310 is equipped with two skin contacting surfaces 311 and 323 positioned at an angle 324 relative to each other. The angle is selected to allow for skin conformance to the adapter when the adapter is applied to the skin surface. The angle has to be below 180 degrees to allow for the adapter needle opening 325 to be positioned in the plane of the skin contact surface 311. This allows for the penetration of the dermis by the needle upon the needle being forwarded from its storage position. It also allows the needle to be advanced into the dermal space in general parallel to the skin surface. The contact surfaces 311 and 323 have been arranged with an area of a gradual transition from surface to surface.

The adapter contact surface 311 covers the welt area formed when the compound is injected. To improve the skin visibility and to allow the skin distension a skin observation window 317 can be formed in the contact surface 311 of the adapter 310.

The adapter 310 and the needle cannula assembly 330 are arranged in a sliding relationship. The adapter 310 has an internal cavity 312 to accommodate the needle assembly 330 and to prevent the exposure of the needle cannula 345 prior and after injection. The needle cannula has a forward tip 348 with a bevel 347. The cannula outer diameter is illustrated as 346 in the attached figures.

The needle cannula assembly 330 has protrusions 336 and 337 to maintain the alignment of the assembly and the adapter 310 during storage, use and in discard position. Furthermore the assembly has a protrusion 333 to maintain the desired bevel 347 position in respect to the skin surface. The protrusion 333 has a proximal slope 334 to accommodate the placement of the assembly into a discard position. The needle cannula is affixed to the hub portion using adhesion, interference fit or any other of the commonly used techniques.

The adapter 310 has two openings, an operation opening 315 and a discard opening 316 to accommodate the needle assembly protrusion 333. During storage and integration with the syringe the protrusion 333 is positioned in the storage opening section 313 of the operation opening 315. The storage opening section 313 is separated from the operation opening 315 by elevations 314. These elevations retain the adapter to needle assembly position prior to needle deployment.

The adapter openings are positioned on a latch 319. The latch 319 is a part of the adapter 310, is separated from the adapter by slits 320 while connected to the body of the adapter at the distal end of the latch. The latch is able to deflect away from the center of the adapter during the integration of the needle cannula assembly 330 with the adapter 310. Furthermore the latch is deflected outward when the protrusion proximal slope impacts the latch bridge 326 during the assembly transition from inject to discard position. Slits 320 also allow the tangential deflection if the side walls of the latch 319 when these are impacted by the protrusion 333.

The dimensions of the adapter cavity 312, the adapter needle opening 325, the outer diameter of the hub portion 331 and protrusions 336 and 337 are selected to assure the forward needle tip is stable and moves parallel to the first contact surface 311 when deployed. Furthermore the adapter has a needle opening cone 321 to assist in the assembly of the adapter and the needle cannula assembly.

The adapter could also have a finger rest 318 for applying some pressure on the surface during the needle insertion into the dermal space. The adapter 310 could also have a recess 327 to minimize the plastic volume. The needle is inserted into the dermal space in general parallel to the skin and the skin contact surface 311. The thickness of the skin layer above the needle is set by the adapter design and the method of use and is illustrated as 322 in FIG. 21.

Figure 19:
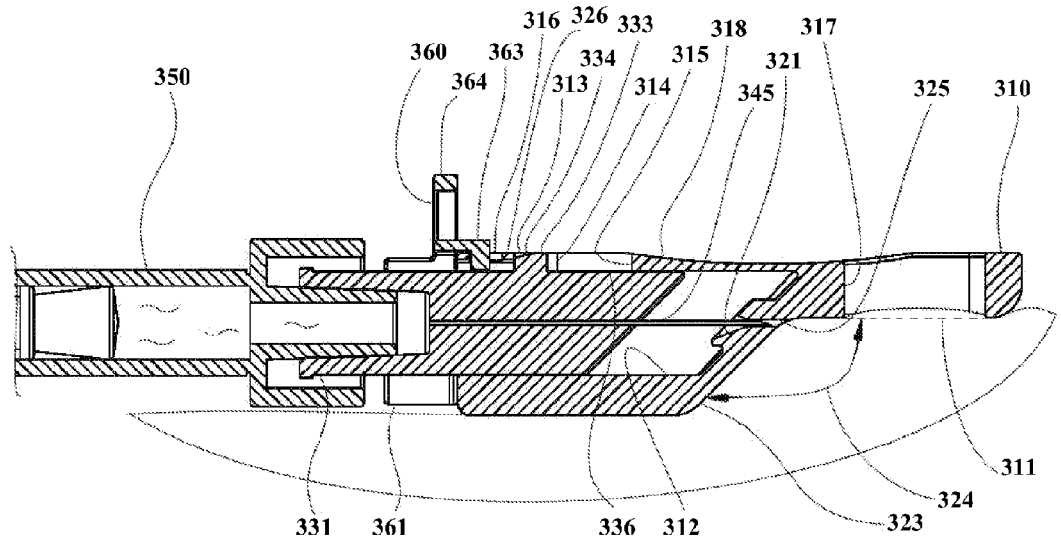
FIG. 19 is a cross sectional view of the device in FIG. 17 as applied to the skin in a pre-insertion position with a partial view of an attached syringe.
Figure 20:
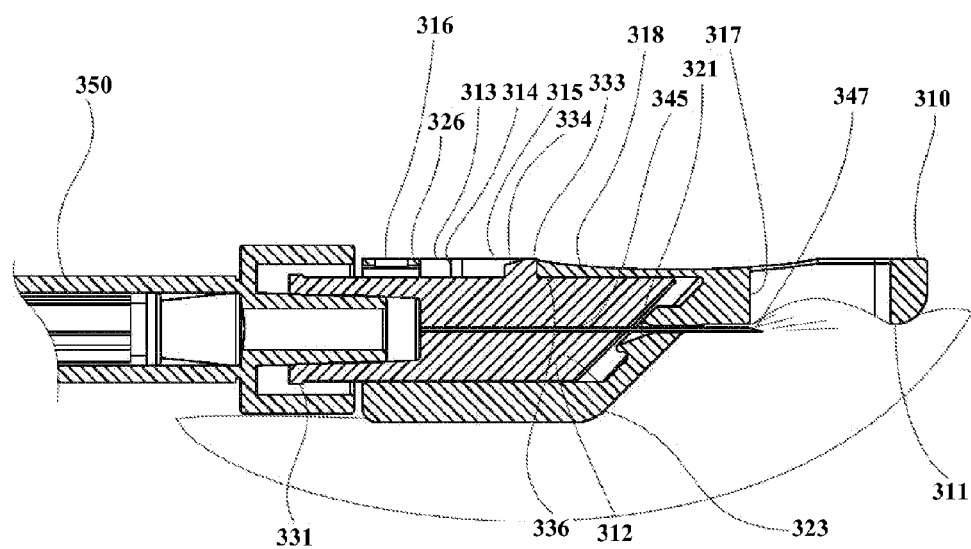
FIG. 20 is a cross sectional view of the device in FIG. 18 during injection after activation with a partial view of an emptied syringe.
Figure 21:
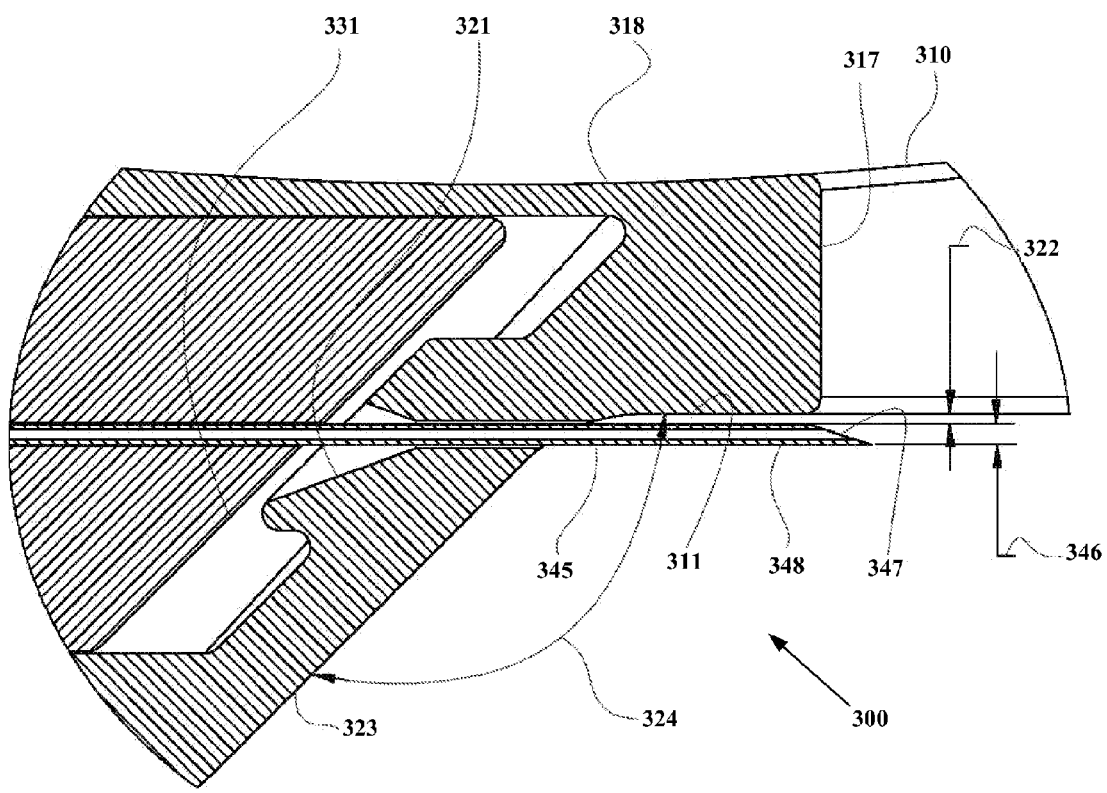
FIG. 21 is an enlarged cross sectional view of the needle area of the device in FIG. 20.
Figure 22:
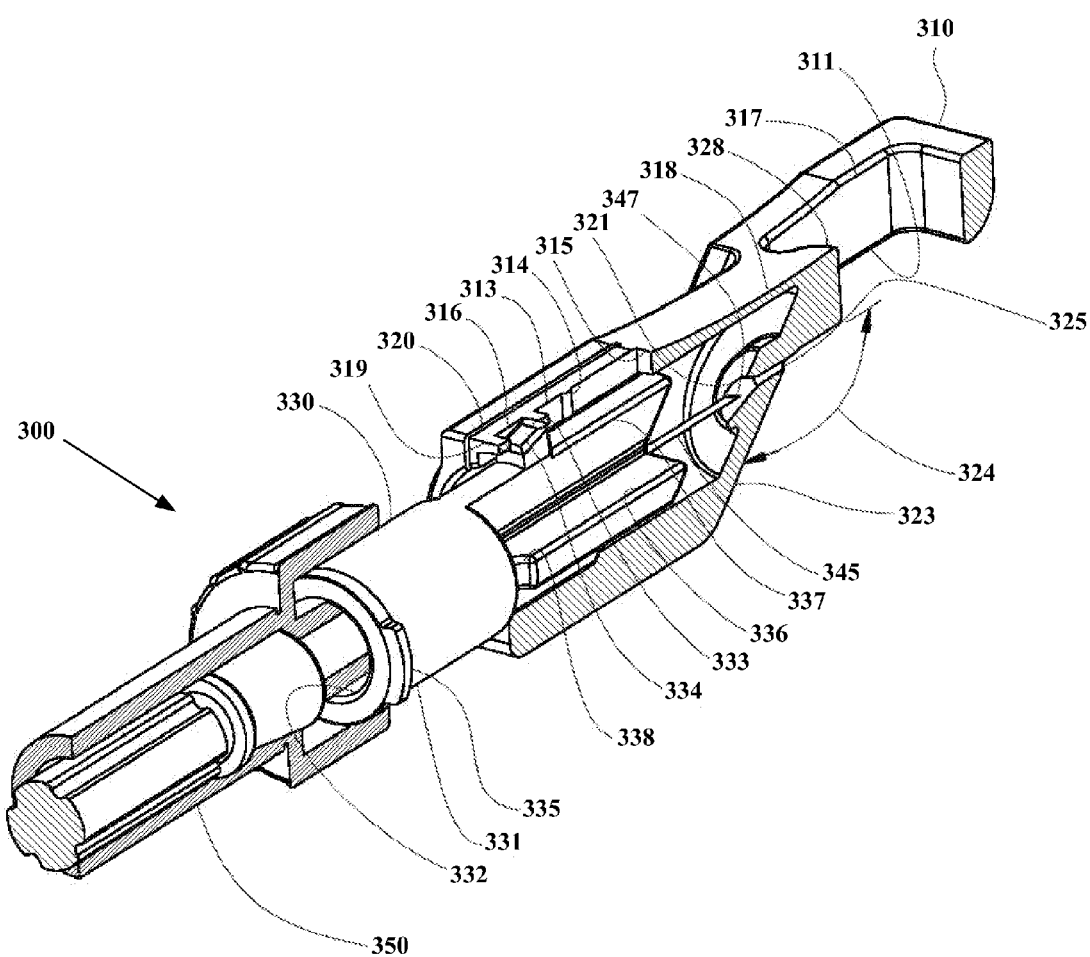
FIG. 22 is a partially cross sectional side perspective view of the syringe and the adapter of the device in FIG. 17 after the needle has been placed into discard position.
Figure 23:
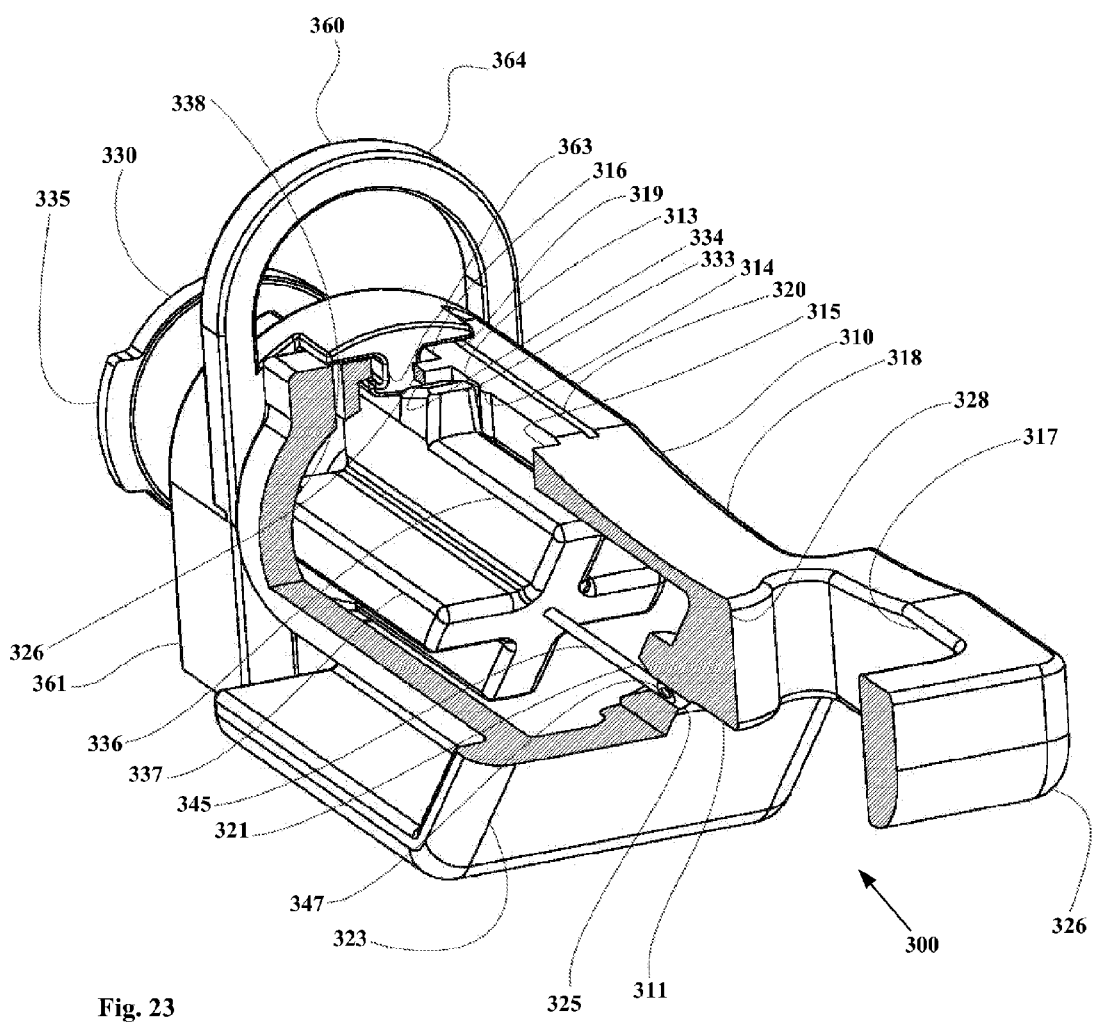
FIG. 23 is an enlarged, cut-away perspective view of the device in FIG. 17 illustrating the safety clip and portions of the adapter in proximity to the safety clip.

Prior to injection the skin tends to slightly bulge and protrude into the window 317 as illustrated in FIG. 19. The window 317 could have an extension 328 to support and prevent bulging of the skin above the needle and to maintain the desired depth of the needle forward tip during needle insertion. The skin will further bulge and protrude into the window during injection as illustrated in FIG. 20.

It is desirable to have a taut skin in contact with the adapter. This is accomplished by the properties of the skin contacting surfaces 311 and 323 and the shape of these surfaces along with the appropriate application techniques. Areas of the skin contacting surfaces could have properties to increase adherence toward skin when the adapter is applied. Furthermore the contacting surfaces could be substantially curved. The part of the adapter contacting surfaces in the plane of the needle (as illustrated in FIG. 19) could be elevated comparing to the peripheral sections of the skin contacting surfaces 311 and 323. These protruding parts of the contact surface would contact the skin during the initial phase of the adapter application resulting in a taut skin.

Figures 18A, 18B:
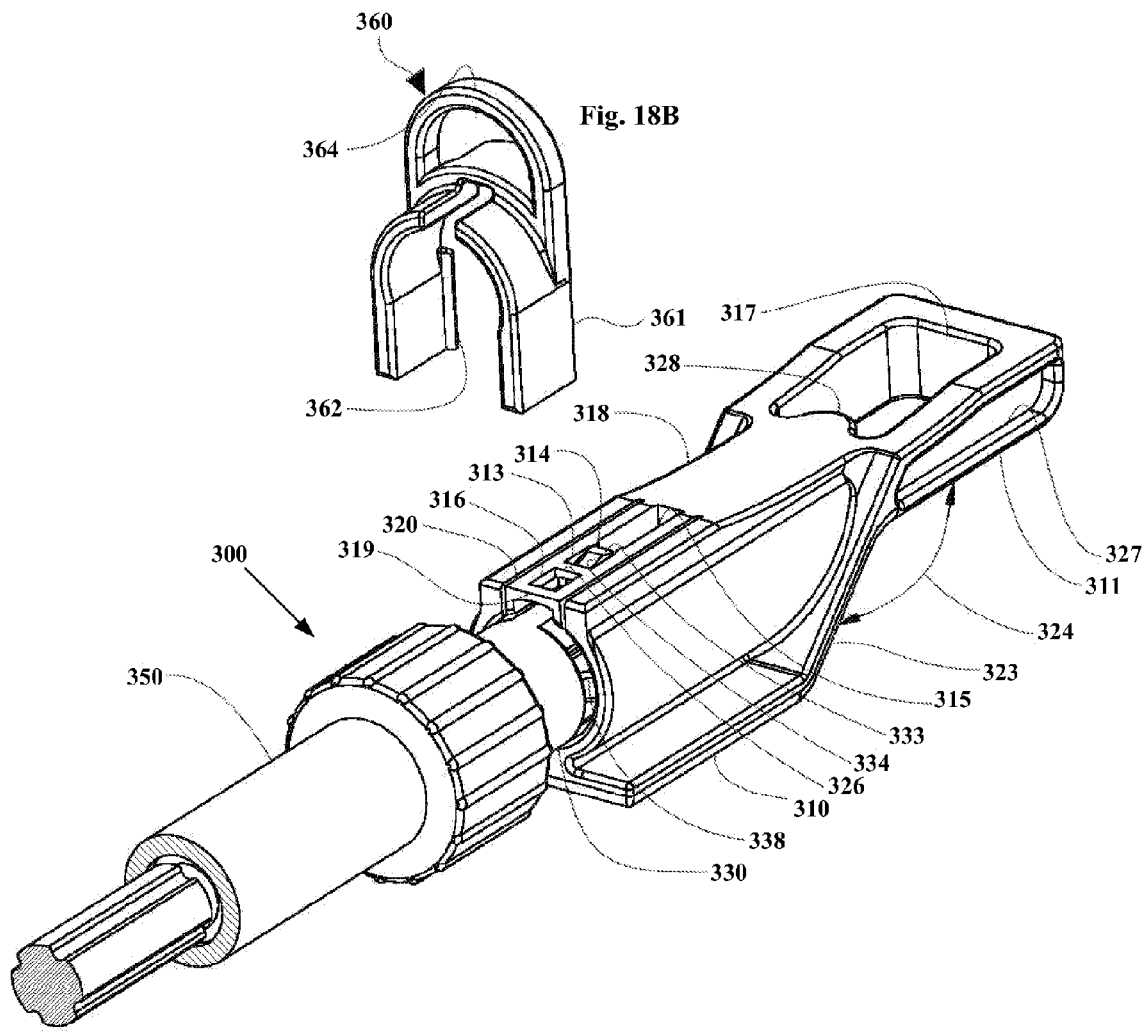
FIG. 18A is a side perspective view of the device in FIG. 17 as merged with a partially illustrated syringe, with the safety clip removed and shown in FIG. 18B.

The needle assembly could be equipped with a safety clip 360 as mentioned above. The safety clip 360 illustrated in FIGS. 17, 18B and 23 has a body 361, ridges 362, clip protrusion 363 and extension 364. The clip is engaged to the needle cannula assembly by ridges 362 interacting with the needle assembly undercuts 338. Furthermore the clip protrusion 363 engages the discard opening 316 of the adapter. The safety clip prevents the relative displacement of the needle assembly and the adapter until the clip removal as illustrated in FIG. 18. The clip can be removed by pulling on the extension 364.

ID injection is substantially simplified when the ID needle assembly is employed. Furthermore, many additional skin sites may be used for intradermal delivery when this needle assembly is used. The assembly assures the injection is consistent in regards to the needle tip placement. The needle assembly is initially connected to the drug delivery device, which may be a pre-filled syringe or a single use syringe filled by the caregiver prior to injection. The system might be primed if required. The needle assembly is applied to the skin at any one of a broad range of suitable sites. These could be conventional sites recommended for ID injection or curved sites offering a curvature compatible with the relative position of the adapter contact surfaces.

The assembly is applied to the skin with some pressure, resulting in tissue deformation and the desired skin compliance with the adapter contact surfaces. The needle is subsequently inserted into the tissue while the contact is maintained. The hub protrusion 333 deflects the latch side walls and is moved into the distal part of the operations opening 315. The needle penetrates into the dermis through the opening 325 in surface 323 and is further advanced substantially parallel to the skin surface.

The compound is expelled from the drug delivery device into the dermis. The injection could take place while the adapter is applied to the skin with some pressure. Alternatively the pressure on the adapter toward the skin could be minimized allowing for more dermis distention and welt formation. Furthermore the adapter could be somewhat elevated above the skin while maintaining the needle tip position in the dermis. This technique could further improve the dermis distension.

The needle could be extracted from the skin while the adapter remains in contact with the dermis. Alternatively the adapter could be removed from the skin with the needle tip exposed and subsequently put into a discard position with the needle being shielded. The placement of the needle assembly into a discard shielded position takes place while the adapter is pushed in the distal direction by a pressure against a table edge or any other protruding element while holding on to the syringe. Subsequently the needle assembly and the syringe are discarded.

Figure 24:
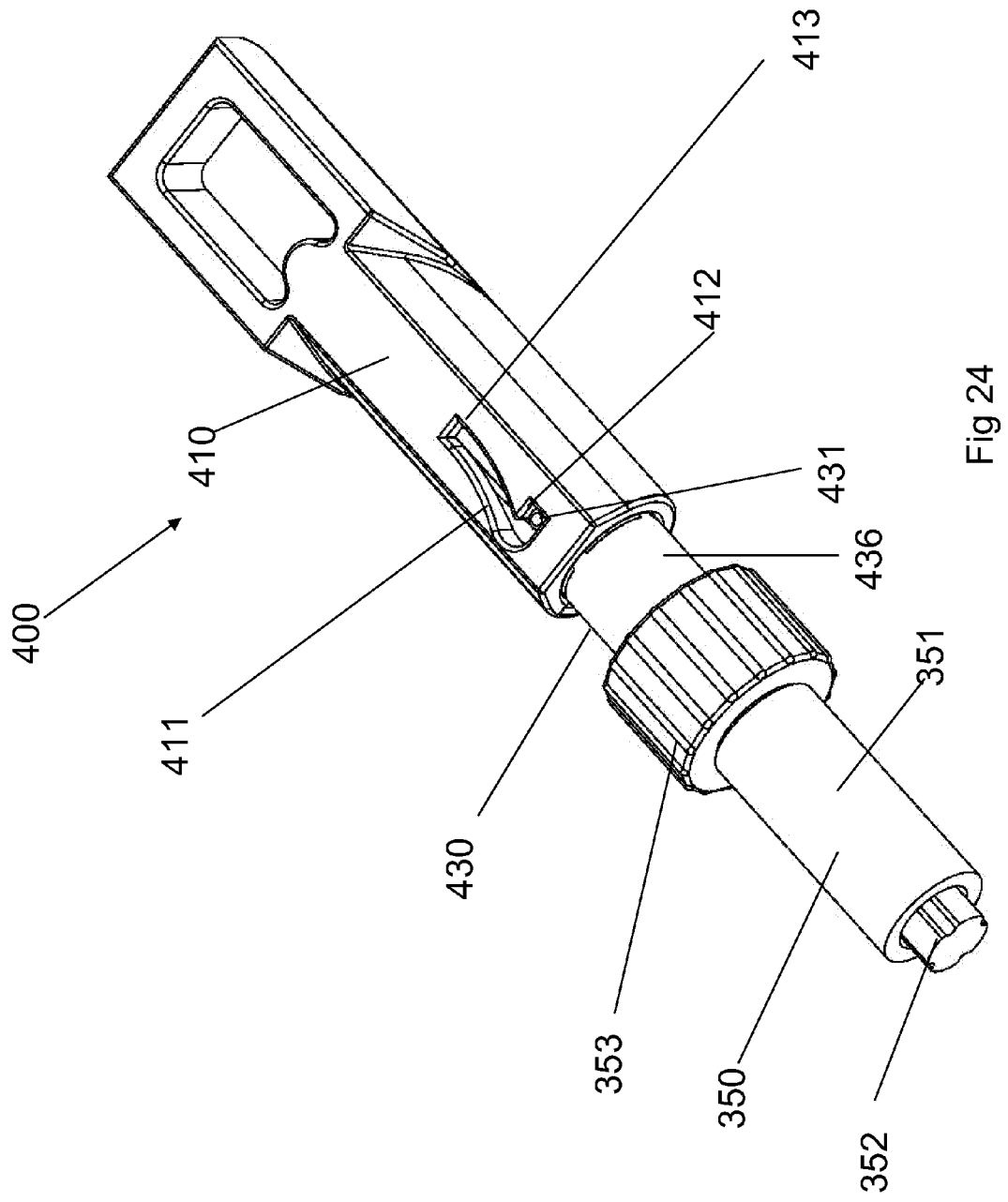
FIG. 24 is a top perspective view of another embodiment of an ID needle assembly according to the invention as merged with a partially illustrated syringe.

Another embodiment 400 is illustrated in FIGS. 24-28. The external view of the embodiment of the device 400 is illustrated in FIG. 24. The main components include an adapter 410 and a needle cannula assembly 430. The needle cannula assembly 430 has a hub 436 retaining the cannula 431. The hub 436 has a protrusion 432 engaging the adapter opening 411. The hub 436 also has another protrusion 433 positioned on a lever 434 and also engaging the adapter 410.

The adapter 410 is in a sliding relationship with the needle cannula assembly 430 and partially surrounds it. The protrusion 432 engages the opening 411 of the adapter 410 whereby in storage the protrusion 432 is positioned at the proximal end 413 of the opening 411. The protrusion 432 and the shape of the proximal end 413 of the opening 411 prevent the distal motion of the needle cannula assembly relative to the adapter during the merger with a luer.

The ID needle 400 is merged with a drug delivery device such as a syringe. The hub of the needle cannula assembly 430 is exposed for merger with say a syringe 350. The syringe has a rod with a stopper 352 and a male luer 354 for merger with the ID needle 400. The syringe could also have a thread component 353 engaging the needle assembly 400 through hub wings 435.

Figure 25:
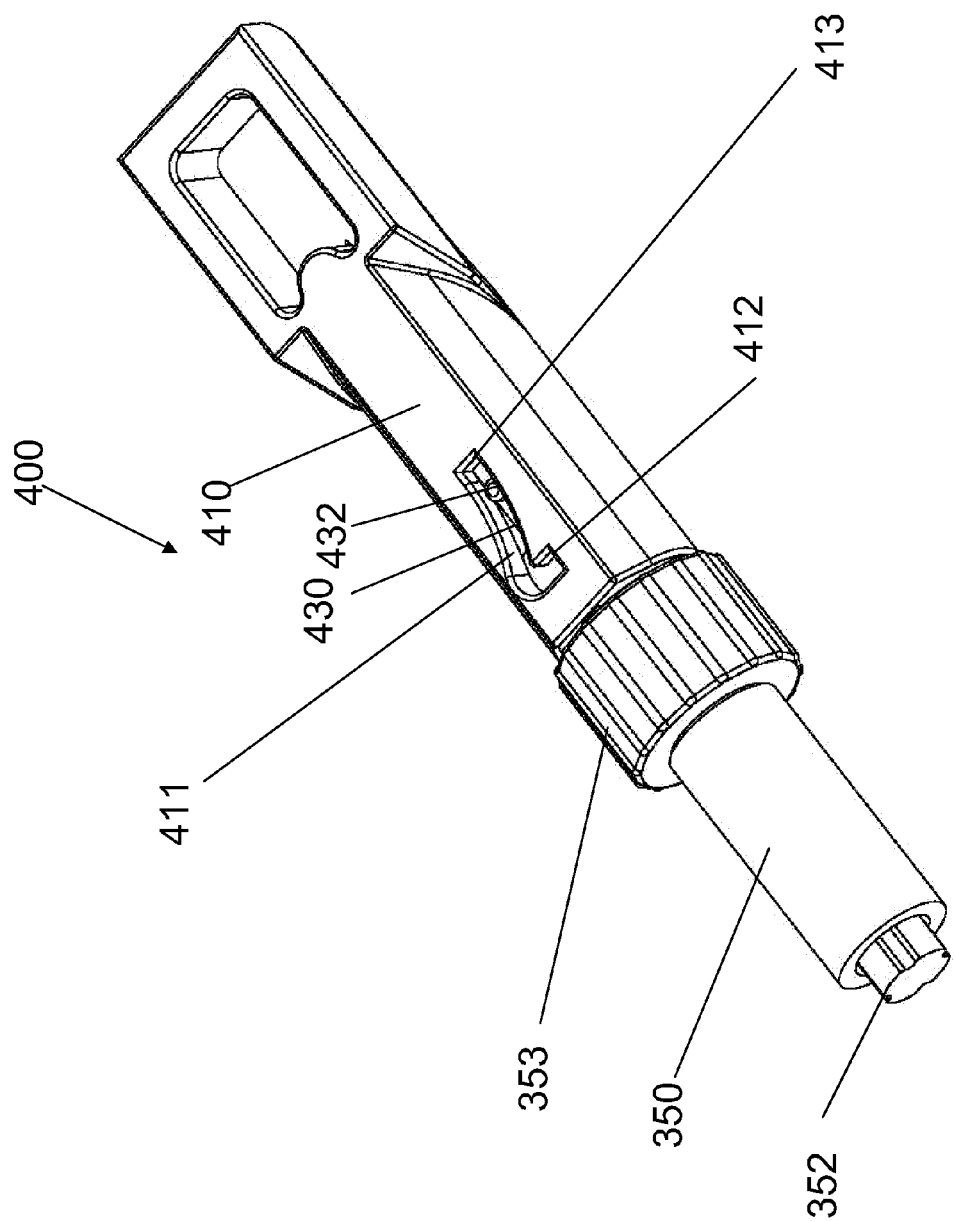
FIG. 25 is a top perspective view of the device of FIG. 24 with the safety clip removed during cannula insertion as merged with a syringe.
Figure 26:
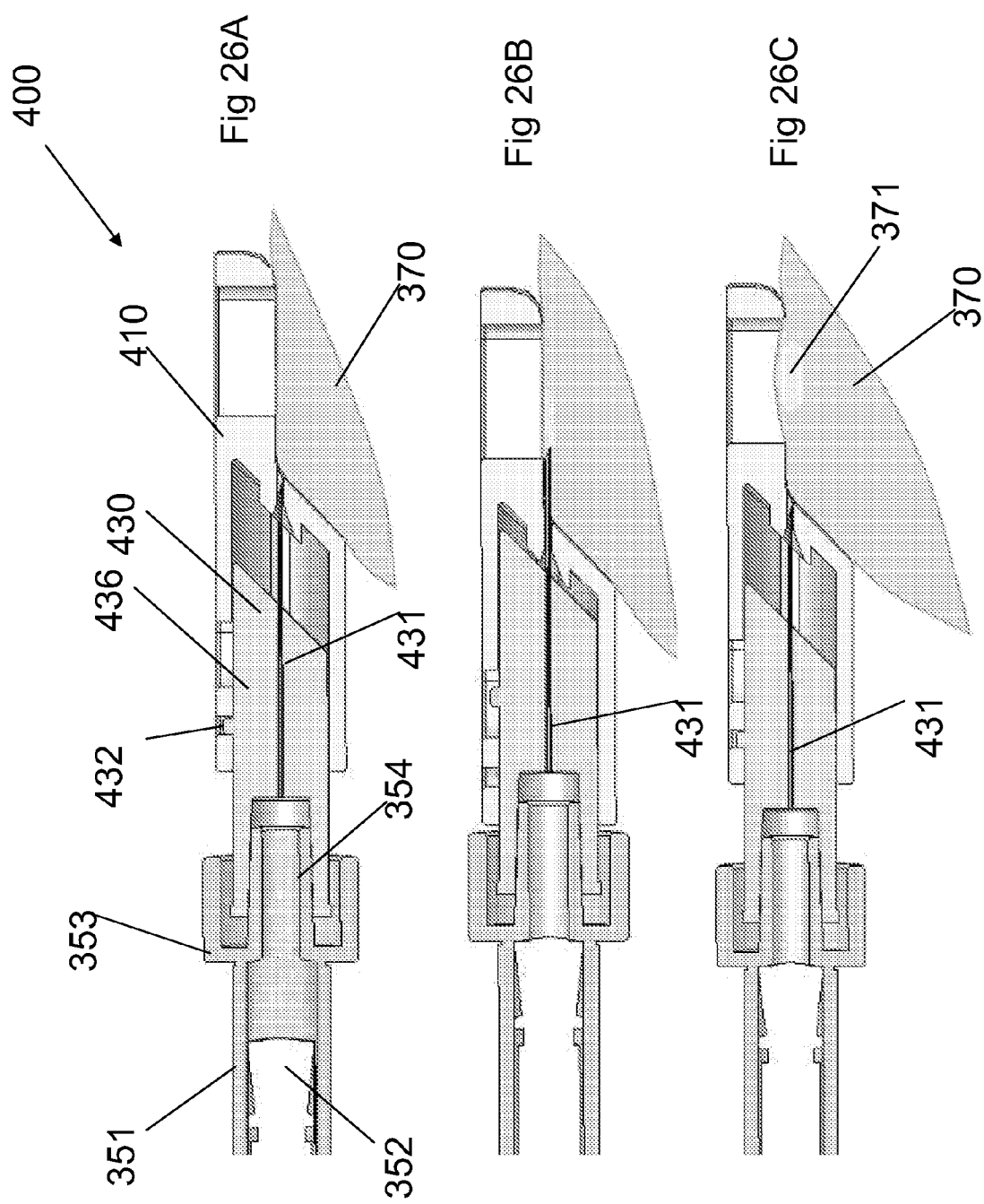
FIGS. 26A-B illustrate cross sectional views of the device in FIG. 24 as merged with a syringe in a pre-insertion position (FIG. 26A), as applied to the skin with the cannula inserted into dermis (FIG. 26B), and after injection with the cannula withdrawn (FIG. 26C)
Figure 27:
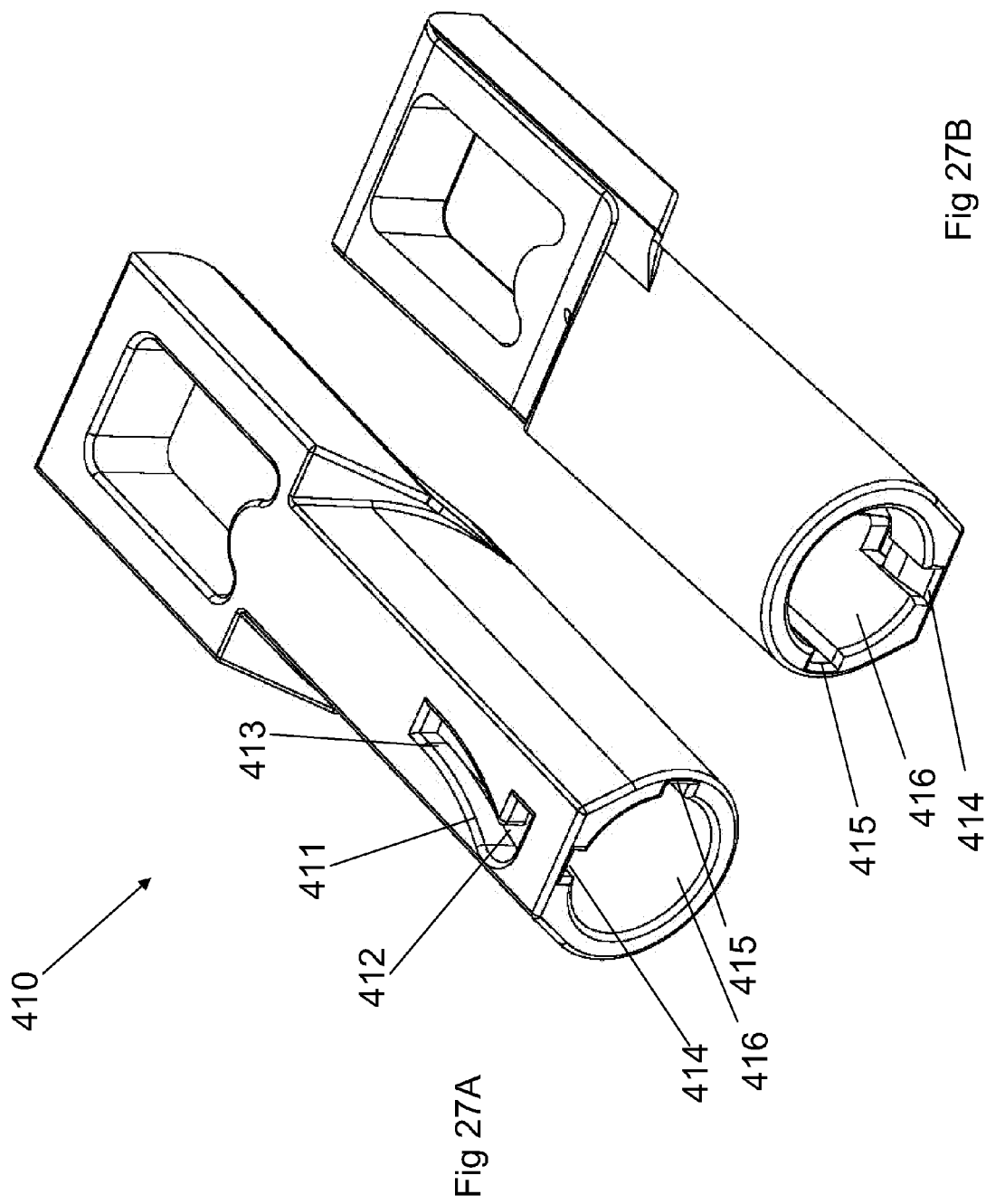
FIGS. 27A-B illustrate perspective views of an adapter of the device of FIG. 24, with a top perspective view shown in FIG. 27A and a bottom perspective view shown in FIG. 27B.
Figure 28:
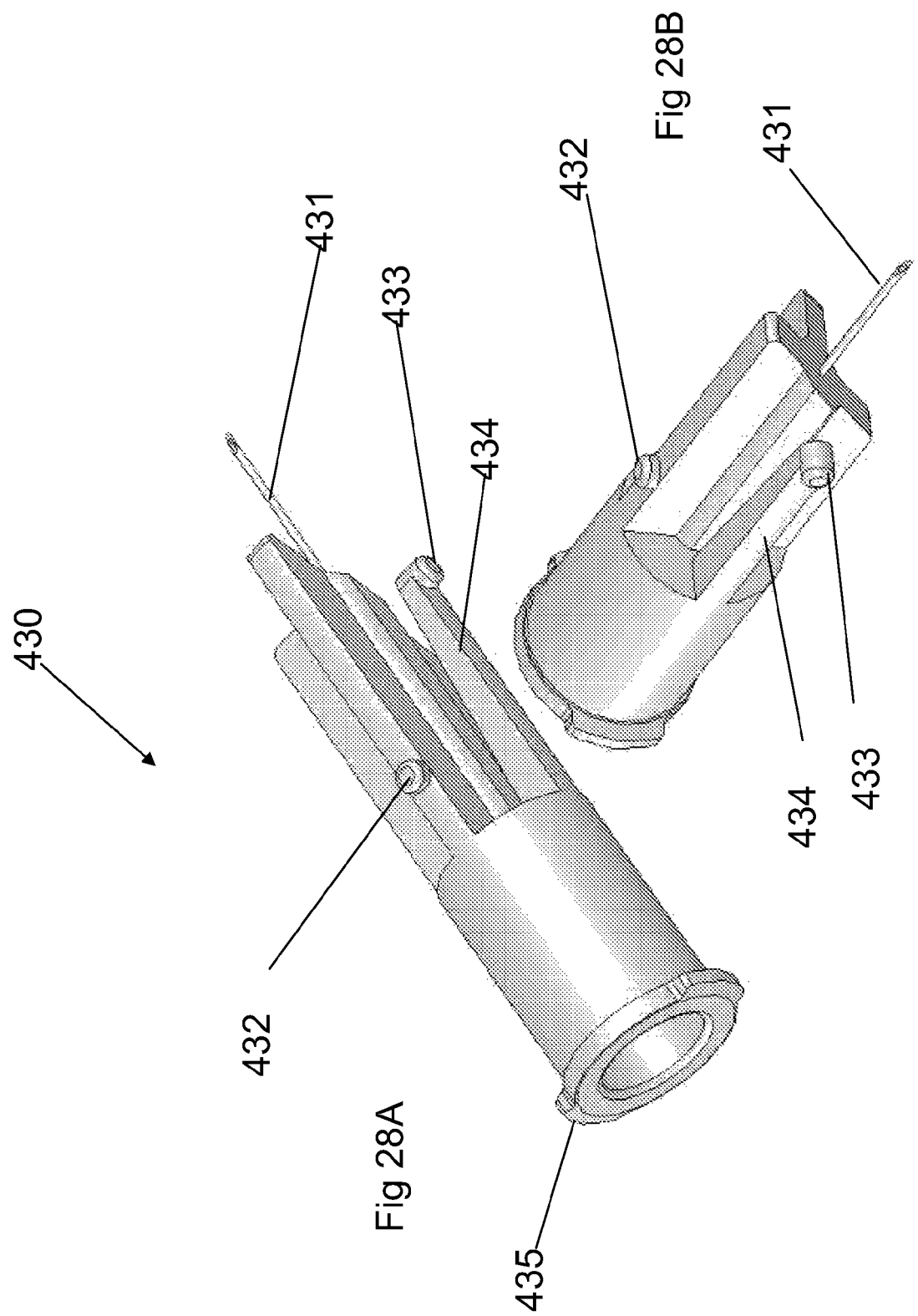
FIGS. 28A-B illustrate perspective views of the cannula assembly of the device of FIG. 24, as viewed facing the luer in FIG. 28A and facing the cannula in FIG. 28B.
Figure 29:
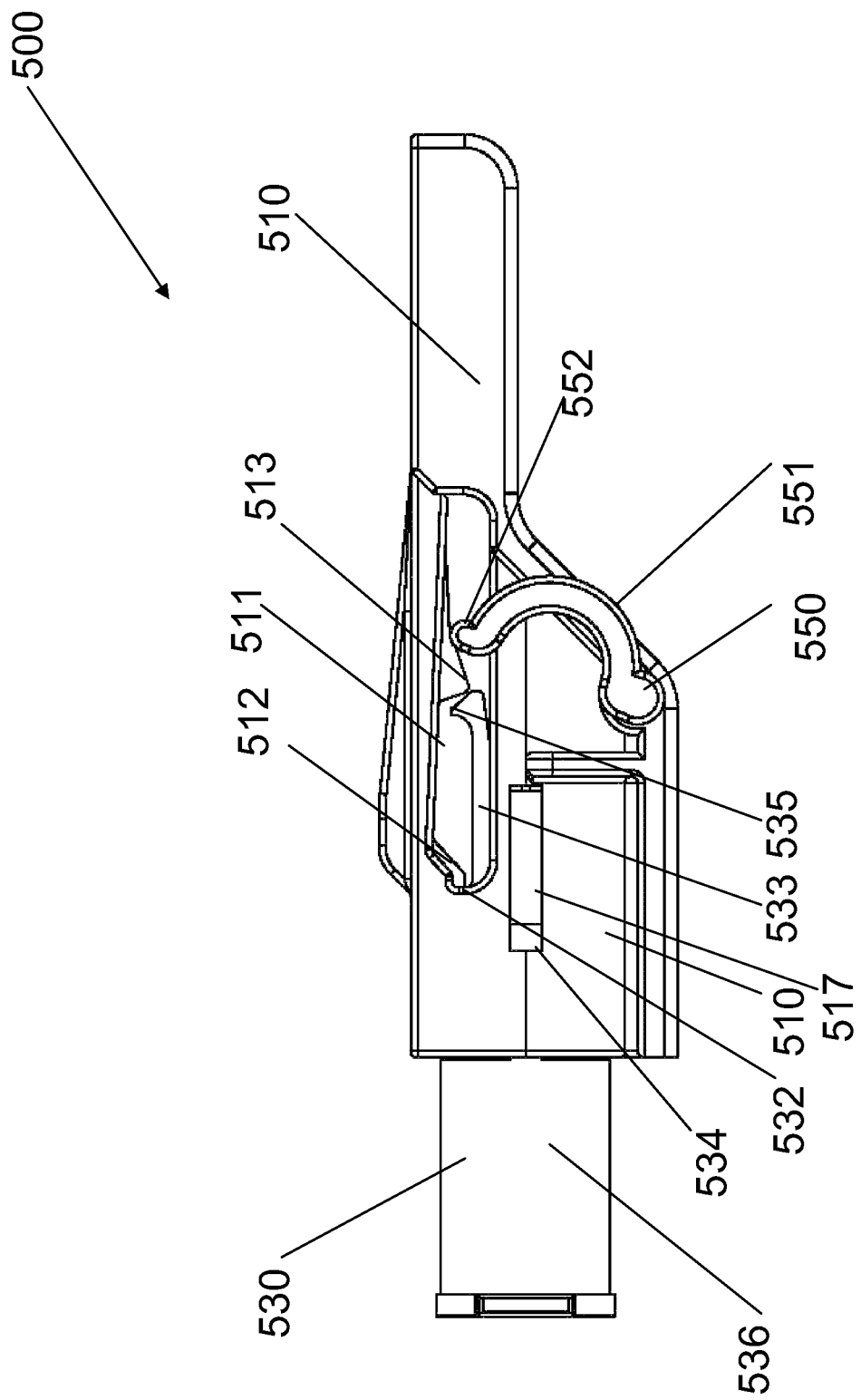
FIG. 29 is a side view of yet another embodiment of an ID needle assembly having a dermis sensor according to the invention.

The assembly is applied to the skin with some pressure, resulting in tissue deformation of the underlying skin and compliance to the adapter contact surfaces. The needle cannula 431 could be inserted into the dermis by slightly turning the needle hub CCW with the protrusion 432 moving along the adapter opening 411. Forward thrust on the syringe after the CCW turn results in the protrusion 432 moving toward the distal end of the adapter opening 412. The cannula position in storage is illustrated in FIG. 26A. At the end of the distal travel the cannula is fully inserted into the dermis 370 as illustrated in FIG. 25 and FIG. 26B. The compound is then injected into dermis forming a drug pool illustrated as 371 in FIG. 26C. The hub protrusion 433 located on the lever 434 of the hub is shown in FIG. 28. In the cannula assembly 410 the protrusion 433 is engaged with an axial slot 415 of the inner adapter cavity 416 of the adapter 410 illustrated in FIG. 27. The lever 434 integral with the hub 436 maintains the cannula and the adapter angular orientation during the device operation. The rotation of the hub in respect to the adapter requires a turning moment to deflect the lever 434. This prevents unintended cannula exposure. The adapter has also another short slot 414 to facilitate the merger of the adapter 410 and the needle cannula assembly 430. The embodiment 400 shields the cannula when not in use preventing needle pricks. This mechanism does not disable the device and allows multiple ID injection as required.

Yet another embodiment of the device 500 is illustrated in FIGS. 29 through 34. The main components include an adapter 510, a needle cannula assembly 530 and a dermis sensor 550. The needle cannula assembly 530 has a hub 536 retaining the cannula 531. The hub 536 has a retention step 532 engaging the adapter lever 211 in storage position. The hub 536 also has an extension 533 with a protrusion 535 positioned on the end of 533.

The adapter 510 is in a sliding relationship with the needle cannula assembly 530 and partially surrounds it. The hub 536 has side protrusions 534 engaging the guiding openings 517 of the adapter 510 whereby in storage the protrusions 534 are positioned at the proximal end of the opening 517. The protrusions 534 and opening 517 assure the angular orientation of the needle cannula assembly 530 relative to the adapter 510 through the device operation. The lever 511 is merged with the adapter 510 through an integral hinge on the proximal end of the lever.

The adapter 510 has a lever 511 as illustrated in FIGS. 29 through 33. The lever has an end protrusion 512 engaging the hub retention step 532 of the cannula assembly 530 during storage and merger with a syringe. The side walls 514 of the lever 511 prevent accidental contact during use.

The dermis sensor 550 has side levers 554 connected by a cross bar 552. The lever pivots 553 engage the adapter 510 through pivot openings 516. The crossbar 552 rests on the bar rest 515 of the adapter 510 when in storage. The dermis contacts the central sections 551 of the side levers 554 of the sensor 550 during the application of the assembly to the skin. The contact forces acting on the side lever section 551 result in the rotation the sensor 550.

Figure 30:
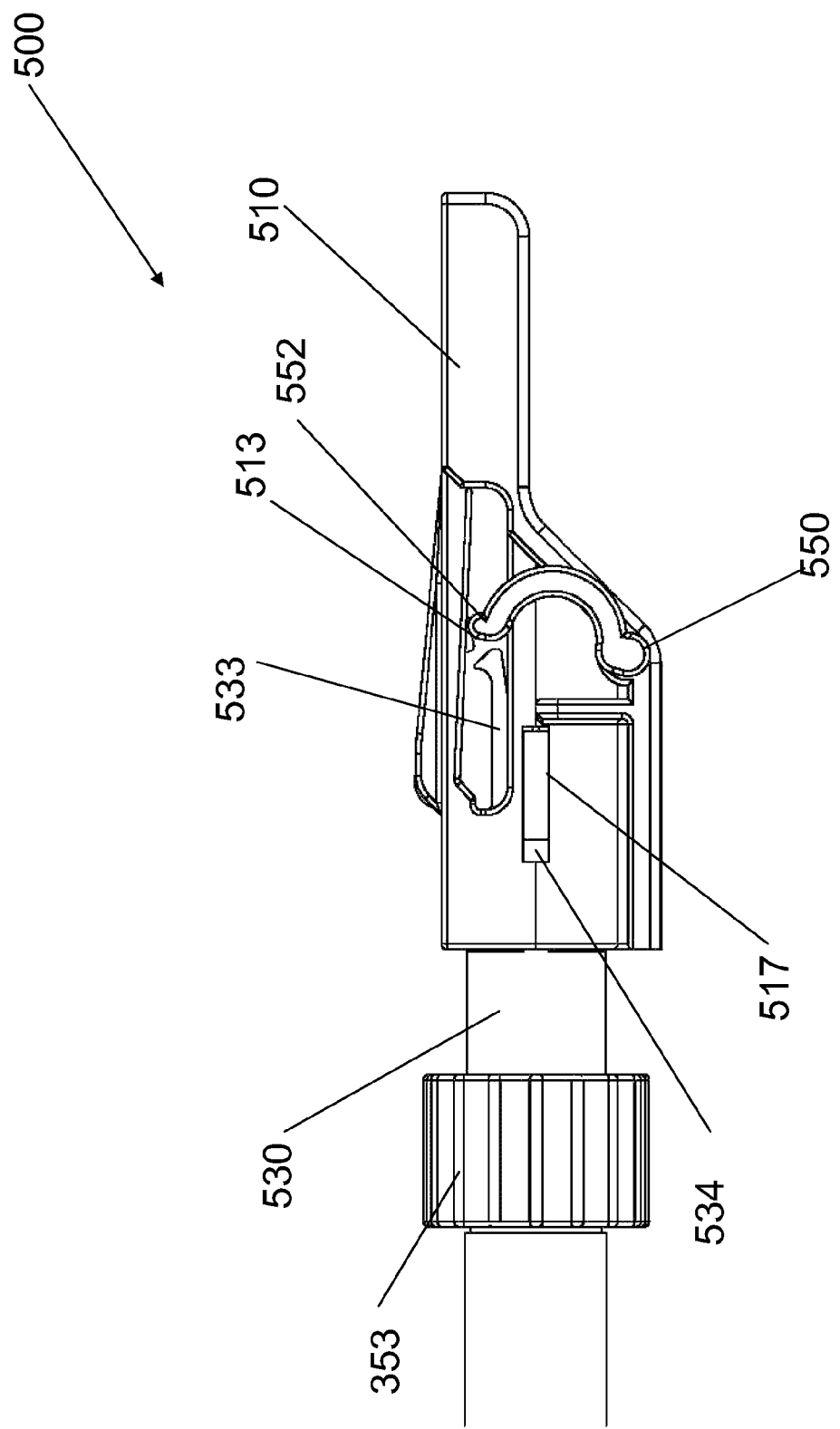
FIG. 30 is a side view of the device in FIG. 29 as merged with a syringe with the sensor turned by the contact with the dermis.

When the needle assembly is applied to the dermis the sensor is rotated by the dermis contact as illustrated in FIG. 30. The cross bar 552 acts on the middle protrusion 513 of the adapter lever 511 and elevates the lever 511. This lever displacement enables the distal motion of the hub 536 and the cannula 531 insertion into dermis 370. The hub 536 is moved forward with the hub extension protrusion 535 bypassing the sensor 550 as shown in FIG. 31.

The sequential injection steps are illustrated in FIG. 32. The lifting of the adapter lever 511 by the bar 552 of the sensor 550 is shown in FIG. 32A. The cannula in then inserted into dermis illustrated as illustrated in FIG. 32B. After injection the cannula assembly is pulled in the proximal direction further rotating the sensor 550 and permanently shielding the needle. The adapter 510 and sensor 550 component designs are shown in FIGS. 33 and 34.

The execution of ID injection is substantially simplified when the ID needle is employed. The tip of the needle cannula is repeatable placed at a desired depth below the dermis surface. Furthermore many additional sites become viable while using the adapter. The adapter could be applied to the skin to any one of the broad range of sites. The assembly assures the injection is consistent in regards to the needle tip placement and compound delivery.

EXAMPLE 1

An ID adapter evaluation was conducted with a machined adapter prototype and a single use syringe. The adapter prototype was sized to accommodate in a sliding relationship BD PLASTIPAK syringe with 1 ml volume, 0.5" long needle and cannula gage 28. The cannula lancet had a conventional subcutaneous bevel. The injection procedure was as follows: 0.1 or 0.5 ml WFI was aspirated into the syringe; the syringe was placed in the adapter with the needle tip positioned in the cannula passageway; the adapter was applied to the desired injection site; the needle was inserted into dermis; the contents were injected; and the needle was withdrawn and the syringe discarded. The needle placement depth was adjusted to locate the cannula center line at about 0.5 mm from the dermis surface. The needle cannula length in the dermis was set at 4.5 mm. WFI volumes of 50 µl and 100 µl were tested.

The initial evaluation in volunteers with the injection of 0.1 ml of WFI produced blebs customarily observed during conventional ID injections. The blebs rapidly diffused. The lancet orientation did not appear to impact the injection results.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

I claim:

1. An adapter (100, 200, 310, 410, 510) for use with a syringe (50, 80, 350) provided with a needle cannula (55, 85, 345, 431, 531) for intradermal injection of a medicament into the skin of a patient comprising:
a body sized to receive in sliding engagement the needle cannula for movement of the needle cannula relative to the body between a first position and a second position;
a first primary skin contacting surface (104, 204, 323) positioned at a distal end of the body and containing an opening sized to receive the needle cannula;
a second primary skin contacting surface (105, 205, 311) positioned at the distal end of the body and further positioned at an angle (123, 223, 324) to the first skin contacting surface between approximately 120 degrees and approximately 165 degrees, the second primary skin contacting surface being fixed with respect to the first primary skin contacting surface and the second primary skin contacting surface being positioned distally with respect to the first primary skin contacting surface; and
a proximal contact surface extending proximally from a proximal end of the first primary skin contacting surface, wherein:
in the first position, the needle cannula is positioned relative to the body such that at least a tip of the needle cannula is retracted within the opening and a longitudinal axis of the needle cannula extends at an angle of greater than 0° and less than 180° with respect to a plane defined by the proximal contact surface;
in the second position, the tip of the needle cannula extends through the opening and the tip of the needle cannula extends outside of the body and exterior to the second skin contacting surface;
in the second position, the needle cannula extends axially in a direction substantially parallel to at least a portion of the second primary skin contacting surface.

2. The adapter of claim 1, further comprising a distal contact surface (116, 216) adjacent the second primary skin contacting surface.

3. The adapter of claim 1, wherein at least a portion of the second primary skin contacting surface is substantially transparent to allow observation of the skin during the injection.

4. The adapter of claim 1, wherein a portion of the second primary skin contacting surface is removed to form an opening through which the skin of the patient may be observed during the injection.

5. The adapter of claim 1, wherein at least one of the first and second primary skin contacting surfaces is grooved to assist in tensioning the skin as the adapter is placed into contact with the patient's skin.

6. The adapter of claim 1, wherein at least one of the first and second primary skin contacting surfaces is formed from a rubbery material that assists in tensioning the patient's skin during the injection.

7. The adapter of claim 1, wherein the first and second primary skin contacting surfaces are configured so that in the second position, the tip of the needle cannula extends into the skin of the patient to a depth measured perpendicularly to the patient's skin surface of between 0.25 mm and 3.0 mm.

8. The adapter of claim 1, wherein a portion of the second primary skin contacting surface is curved.

9. The adapter of claim 1, wherein the body, including the first and second primary skin contacting surfaces, and needle cannula are configured such that in the second position, approximately 1.0 to 8.0 mm of the needle cannula extends into the skin of the patient.

10. The adapter of claim 1, wherein an undercut (94) formed in a hub (93) of the syringe is positioned to engage a first latch (213) of the adapter to hold the syringe in the first position.

11. The adapter of claim 10, wherein following the injection, the tip of the needle cannula is permanently shielded within the body and the syringe is locked in position relative to the adapter by engagement of the first latch (213) and a second latch (232) with the hub undercut.

12. The adapter of claim 1, wherein:
the needle cannula is provided as part of a needle cannula assembly (330, 430, 530) slidably connected to the adapter, and
the needle cannula assembly includes a hub (331, 436, 536) sized and shaped to mate with a fitting on the syringe.

13. The adapter of claim 12, wherein the hub includes a first radial protrusion (433) and the body has a matching axial opening (415) to control angular orientation of the hub relative to the adapter in movement from the first position to the second position.

14. The intradermal needle assembly of claim 13, further comprising a clip retainer that prevents accidental activation of the intradermal needle assembly during merger with a drug delivery device.

15. The intradermal needle assembly of claim 13, wherein the needle cannula assembly comprises two protrusions arranged to slide in openings of the adapter wherein one protrusion of the needle cannula assembly is flexibly attached to the needle cannula assembly body and one protrusion is rigidly fixed to the needle cannula assembly body.

16. The intradermal needle assembly of claim 15, wherein engagement of the rigidly fixed protrusion in the adapter opening prevents distal motion of the needle hub during merger with a drug delivery device and guides the cannula assembly distally for the cannula insertion when the needle cannula assembly is rotated in respect to the adapter.

17. The intradermal needle assembly of claim 13, additionally comprising an integral dermis sensor that prevents relative component displacement during merger with a drug delivery device and prior to needle cannula application to the dermis.

18. The intradermal needle assembly of claim 17, wherein the integral dermis sensor is activated while the adapter is applied to the injection site enabling the cannula insertion.

19. The intradermal adapter of claim 17, wherein the integral dermis sensor is captured by a protrusion of the intradermal cannula assembly upon cannula withdrawal with the cannula permanently shielded.

20. The adapter of claim 12, wherein the hub includes a second radial protrusion (432) and the body has a matching axial opening (411) which prevents distal motion of the syringe during assembly of the needle cannula assembly and the syringe.

21. The adapter of claim 12, further comprising a rotatable dermis sensor element (551) and a latching element (511) in cooperative engagement with the needle cannula assembly, wherein:
the dermis sensor and latching element are biased into a first configuration blocking distal movement of the needle cannula assembly;
upon contact of the dermis sensor with the patient's skin, the dermis sensor and latching element are moved into a second configuration allowing distal movement of the needle cannula assembly.

22. The adapter of claim 21, wherein following the injection and upon movement of the needle cannula assembly in a proximal direction, the dermis sensor is further rotated into a position such that the latching element is moved to a position blocking distal movement of the needle cannula.

23. The intradermal needle assembly of claim 22, wherein the needle cannula is permanently shielded by the needle cannula assembly being moved into a discard position of the adapter wherein the protrusion proximal slope elevates the latch to move the protrusion into the second latch opening.

24. A method of making an intradermal injection into the skin comprising the steps of:
providing an intradermal needle assembly comprising a needle cannula with a forward needle tip and an integral adapter surrounding the needle cannula, the adapter having a first skin contacting surface, a second skin contacting surface, and a proximal contact surface extending proximally from a proximal end of the first skin contacting surface, the needle cannula being in fluid communication with a drug delivery device, a longitudinal axis of the needle cannula extending at an angle of greater than 0° and less than 180° with respect to a plane defined by the proximal contact surface, the first and second skin contacting surfaces being positioned at a distal end of the assembly, the second skin contacting surface being positioned distally with respect to the first skin contacting surface;
engaging the first and second skin contacting surfaces and the proximal contact surface with the skin;
inserting the needle cannula into the dermis layer of the skin through an opening in the first skin contacting surface, wherein the needle cannula is further inserted in the dermis generally parallel to the second skin contacting surface;
expelling a fluid from the drug delivery device into the dermis; and
removing the intradermal needle assembly from the skin.

25. The method of claim 24 wherein pressure on the skin is minimized while the fluid is expelled from the drug delivery device.

26. The method of claim 24 wherein the needle is shielded after removal of the intradermal needle assembly from the skin.

27. The method of claim 24 wherein the intradermal needle assembly is withdrawn from the skin prior to the removal of the needle adapter from the tissue.

28. The method of claim 24 wherein a safety clip maintains the needle assembly in position relative to the adapter during the merger of the intradermal needle assembly with the drug delivery device.

29. A method of making an intradermal injection into the skin comprising the steps of:
providing an intradermal needle assembly having a forward needle tip and an integral adapter surrounding the needle cannula, the adapter having two surfaces for contacting the skin and the needle cannula being in fluid communication with a drug delivery device;
engaging the contact surfaces of the adapter with the skin and maintaining contact of the skin with both adapter contact surfaces;
slightly turning a needle hub counterclockwise as defined by a hub pin position to enable distal travel of the hub;
inserting the needle into the dermis layer of the skin through an opening in one of the contact surfaces, wherein the needle cannula enters the dermis through the first surface and is further inserted in general parallel to the skin surface;
expelling the compound from the drug delivery device into the dermis; and removing, shielding, and discarding the needle assembly.

30. A method as set forth in claim 29 wherein a hub protrusion of the cannula assembly positioned in an adapter opening prevents distal movement of the cannula assembly during the merger of the intradermal needle assembly with the drug delivery device.

31. A method of making an intradermal injection into the skin comprising the steps of:
providing an intradermal needle assembly having a forward needle tip, an integral adapter surrounding the needle cannula and a dermis sensor, the adapter having two surfaces for contacting the skin and the needle cannula being in fluid communication with a drug delivery device;
engaging the contact surfaces of the adapter with the skin and maintaining contact of the skin with both adapter contact surfaces;
activating the dermis sensor while contacting the skin and maintaining the contact;
inserting the needle into the dermis layer of the skin through an opening in one of the contact surfaces, wherein the needle cannula enters the dermis through the first surface and is further inserted generally parallel to the skin surface;
expelling the compound from the drug delivery device into the dermis; and
removing and shielding the cannula whereby the assembly is permanently disabled for safe discard.

32. A method as set forth in claim 31 wherein the dermal sensor prevents distal movement of the cannula assembly during the merger of the intradermal needle assembly with the drug delivery device and permanently disables the assembly after use.

33. A method for providing an intradermal injection, comprising:
- contacting a skin surface with first and second skin contacting surfaces and a proximal contact surface of an adapter device having a drug delivery device mounted in an internal cavity, the first and second skin contacting surfaces being arranged at an angle of less than 180° relative to one another, the first and second skin contacting surfaces being positioned at a distal end of the assembly, the second skin contacting surface being positioned distally with respect to the first skin contacting surface, the proximal contact surface extending proximally from a proximal end of the first skin contacting surface;
- inserting a needle cannula of the drug delivery device through an opening in the adapter device and into the skin, a longitudinal axis of the needle cannula extending at an angle of greater than 0° and less than 180° with respect to a plane defined by the proximal contact surface; and
- extending the needle cannula into the dermal layer along a path generally parallel to and below the second skin contacting surface.

* * * * *